(12) United States Patent
Fan et al.

(10) Patent No.: US 10,604,586 B2
(45) Date of Patent: Mar. 31, 2020

(54) HUMANIZED MONOCLONAL ANTIBODY AND USES THEREOF

(71) Applicant: Industrial Technology Research Institute, Hsinchu (TW)

(72) Inventors: Chia-Yu Fan, Hsinchu (TW); Min-Yuan Chou, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 71 days.

(21) Appl. No.: 15/589,191

(22) Filed: May 8, 2017

(65) Prior Publication Data

US 2017/0320966 A1 Nov. 9, 2017

Related U.S. Application Data

(60) Provisional application No. 62/333,339, filed on May 9, 2016.

(30) Foreign Application Priority Data

Dec. 28, 2016 (TW) .............................. 105143525 A

(51) Int. Cl.
| | |
|---|---|
| *C07K 16/28* | (2006.01) |
| *A61K 39/44* | (2006.01) |
| *A61K 39/395* | (2006.01) |
| *A61K 47/69* | (2017.01) |
| *A61K 47/68* | (2017.01) |
| *C07K 16/46* | (2006.01) |
| *C07K 16/18* | (2006.01) |
| *C07K 19/00* | (2006.01) |
| *A61K 39/00* | (2006.01) |

(52) U.S. Cl.
CPC .............. *C07K 16/46* (2013.01); *A61K 39/44* (2013.01); *C07K 16/18* (2013.01); *C07K 16/28* (2013.01); *C07K 16/2896* (2013.01); *C07K 16/462* (2013.01); *C07K 19/00* (2013.01); *A61K 39/0011* (2013.01); *A61K 2039/5152* (2013.01); *C07K 2317/24* (2013.01); *C07K 2317/73* (2013.01); *C07K 2317/76* (2013.01); *C07K 2317/92* (2013.01); *C07K 2317/94* (2013.01)

(58) Field of Classification Search
CPC .. C07K 16/462; C07K 16/2896; C07K 16/18; C07K 2317/24; C07K 2317/76; A61K 39/44; A61K 2039/505; A61K 47/6929; A61K 47/6933; A61K 47/6877; A61K 47/6898; A61K 47/6849
See application file for complete search history.

(56) References Cited

U.S. PATENT DOCUMENTS

| | | |
|---|---|---|
| 8,883,738 B2 | 11/2014 | Matzke et al. |
| 8,927,696 B2 | 1/2015 | Chiu et al. |
| 9,035,027 B2 | 5/2015 | Ghayur et al. |
| 9,095,580 B2 | 8/2015 | Isner et al. |
| 2013/0172533 A1 | 7/2013 | Chiu et al. |

FOREIGN PATENT DOCUMENTS

| | | |
|---|---|---|
| CN | 101481417 A | 7/2009 |
| EP | 2 233 501 A1 | 9/2010 |
| TW | 201326203 A1 | 7/2013 |
| TW | I443107 B | 7/2014 |
| WO | WO 2016/049036 A1 | 3/2016 |

OTHER PUBLICATIONS

Rudikoff et al., PNAS 79: 1979-1983 (Year: 1982).*
Chen et al., EMBO J., 14: 2784-2794 (Year: 1995).*
Stancovski et al., PNAS, 88: 8691-8695 (Year: 1991).*
Jiang et al., J. Biol. Chem. 280 (6): 4656-4662 (Year: 2005).*
Fan et al., "De Novo Protein Sequencing, Humanization and in Vitro Effects of an Antihuman CD34 Mouse Monoclonal Antibody," Biochemistry and Biophysics Reports, vol. 9, 2017 (published online Nov. 18, 2016), pp. 51-60.
Rickert et al., "Combining Phage Display with De Novo Protein Sequencing for Reverse Engineering of Monoclonal Antibodies," mAbs, vol. 8, No. 3, Feb. 6, 2016, pp. 501-512.
Taiwanese Office Action and Search Report for Taiwanese Application No. 105143525, dated Aug. 15, 2017.
European Search Report for Appl. No. 17170095.8 dated Sep. 5, 2017.

(Continued)

*Primary Examiner* — Phuong Huynh
(74) *Attorney, Agent, or Firm* — Birch, Stewart, Kolasch & Birch, LLP

(57) ABSTRACT

A humanized monoclonal antibody against the CD34 surface antigen is provided in the present disclosure. The humanized monoclonal antibody includes a light chain variable region and a heavy chain variable region. In which, a nucleotide sequence encoding the amino acid sequence for the light chain variable region comprises a nucleotide sequence which encodes the amino acid sequence of SEQ ID No. 9 or an amino acid sequence with at least 80% sequence identity to the sequence of SEQ ID No. 9, and a nucleotide sequence encoding the amino acid sequence for the heavy chain variable region comprises a nucleotide sequence which encodes the amino acid sequence of SEQ ID No. 10 or an amino acid sequence with at least 80% sequence identity to the sequence of SEQ ID No. 10.

16 Claims, 15 Drawing Sheets
Specification includes a Sequence Listing.

(56) References Cited

OTHER PUBLICATIONS

Padlan, E.A., et al, "A Possible Procedure for Reducing the Immunogenicity of Antibody Variable Domains While Preserving Their Ligand-Binding Properties," Molecular Immunology, 1991, vol. 28, No. 4/5, pp. 489-498.

Pham, V., et al, "De novo proteomic sequencing of a monoclonal antibody raised against OX40 ligand," Analytical Biochemistry, 2006, vol. 352, pp. 77-86.

Berenson et al., "Antigen CD34+Marrow Cells Engraft Lethally Irradiated Baboons", The Journal of Clinical Investigation, vol. 81, No. 3, 1988, pp. 951-955.

Clark, Mike, "Antibody humanization: a case of the 'Emperor's new clothes?'", Immunology Today, vol. 21, No. 8, Aug. 2000, pp. 397-402.

Eskander et al., "Bevacizumab in the treatment of ovarian cancer", Biologics: Targets and Therapy, vol. 5, 2011, pp. 1-5.

Kato et al., "Isolation and Characterization of CD34+Hematopoietic Stem Cells From Human Peripheral Blood by High-Gradient Magnetic Cell Sorting", Cytometry, vol. 14, No. 4, 1993, pp. 384-392.

Mackie et al., "CD34-Positive Stem Cells in the Treatment of Heart and Vascular Disease in Human Beings", Texas Heart Institute Journal, vol. 38, No. 5, 2011, pp. 474-485.

Maltby et al., "Opposing Roles for CD34 in B16 Melanoma Tumor Growth Alter Early Stage Vasculature and Late Stage Immune Cell Infiltration", PLoS One, vol. 6, Issue 4, Apr. 2011, e18160, pp. 1-10.

Nielsen et al., "Novel functions of the CD34 family", Journal of Cell Science, vol. 121, No. 22, 2008, pp. 3683-3692.

Siemerink et al., "CD34 marks angiogenic tip cells in human vascular endothelial cell cultures", Angiogenesis, vol. 15, No. 1, 2012, pp. 151-163.

Simmons et al., "Molecular cloning of a cDNA encoding CD34, a sialomucin of human hematopoietic stem cells", The Journal of Immunology, vol. 148, No. 1, Jan. 1, 1992, pp. 267-271.

\* cited by examiner

Trypsin + Glu-C (SEQ ID NO: 58)
1 QLVLTQSSSA SFSLGASAKL TCTLSSQHRT FTIEWYQQQP LKPPKXXXXX XXDGSHSTGD
Trypsin (SEQ ID NO: 59)
1 QLVLTQSSSA SFSLGASAKL TCTLSSQHRT FTIEWYQQQP LKPPKYVMEL RKDGSHSTGD
In-gel Trypsin (SEQ ID NO: 60)
1 QLVLTQSSSA SFSLGASAKL TCTLSSQHRT FTIEWYQQQP LKPPKYVMEL RKDGSHSTGD
Glu-C (SEQ ID NO: 61)
1 QLVLTQSSSA SFSLGASAKL TCTLSSQHRT FTIEXXXXXX XXXXXXXXXX XXXXXXXXXX
Chymotrypsin (SEQ ID NO: 62)
1 QLVLTQSSSA SFSLGASAKL TCTLXXXXXX XXXXXXQQQP LKPPKYVMEL RKDGSHSTGD
Thermolysin (SEQ ID NO: 63)
1 QLVLTQSSSA SFSLGASAKL XXXXLSSQHRT FTIEXXQQQP LKPPKYXXXL RKDGSHSTGD
Subtilin (SEQ ID NO: 64)
1 QLVLTQSSSA SFSLGASAKX TCTLSSQHRT FTIEXXQQQP LKPPKYVXXX RKDGSHSTGD Trypsin + Glu-C (SEQ ID NO: 58)
61 GIPDRXXXXX XXXXXYLSIS NIQPEDEAIY ICGVGNTIKE QFVYVFGGGT KVTVLGQPKS
Trypsin (SEQ ID NO: 59)
61 GIPDRFSGSS SGADRYLSIS NIQPEDFAIY ICGVGNTIKE QFVYVFGGGT KXXXXXXXXS
In-gel Trypsin (SEQ ID NO: 60)
61 GIPDRFSGSS SGADRYLSIS NIQPEDFAIY ICGVGNTIKE QFVYVFGGGT KVTVLGQPKS
Glu-C (SEQ ID NO: 61)
61 XXXXXXXXXX XXXXXXXXXX XXXXXDEAIY ICGVGNTIKE QFVYVFGGGT KVTVLGQPKS
Chymotrypsin (SEQ ID NO: 62)
61 GIPDRFSGSS SGADRYLSIS NIQPEDEAIY ICGVGNTIKE QFVYVFGGGT XXXXXXXXXX
Thermolysin (SEQ ID NO: 63)
61 GIPDRFSGSS SGADRYXXXX XXXXXXXXXX XXXXXXXXXX XXXXVFGGGT KVTVLGQPKS
Subtilin (SEQ ID NO: 64)
61 GIPDRFSGSX XXXXXYLSIS NIQPEDEAIY ICGVGNTIKX XXXXXXXXXX XXXXXXXXXS

Fig. 3A

Trypsin + Glu-C (SEQ ID NO: 65)
  1 QVQLEQSGPE LVKPGASVKX XXXASGYTFT SYVIHWVKQK PGQGLEWLGY TNPYNDVTKX Trypsin (SEQ ID NO: 66)
  1 QVQLEQSGPE LVKPGASVKX XXXXSGYTFT SYVIHWVKQK PGQGLEWLGY TNPYNDVTKY In-gel Trypsin (SEQ ID NO: 67)
  1 QVQLEQSGPE LVKPGASVKM SCKASGYTFT SYVIHWVKQK PGQGLEWLGY TNPYNDVTKY Glu-C (SEQ ID NO: 68)
  1 XXXXXXXXXX XXXXXXXXXX XXXXXXXXXX XXXXXXXXXX XXXXXWLGY TNPYNDVTKY Chymotrypsin (SEQ ID NO: 69)
  1 XXXXXXXXXX XXXXXXXXXX XXXXXXXXXX XXXXXXXXXX XXXXXXXGY TNPYNDVTKY Thermolysin (SEQ ID NO: 70)
  1 XXXXXXXXXX XXXXXXXXXX XXXXASGYTFT SYVIHWVKXX XXXXXXXXXX XXXXXXXXXX Subtilin (SEQ ID NO: 71)
  1 XXXXXQSGPE LVKRGASXXX XXXASGYTFT SYVIHWVKXX XXXXXXXXXX XXXXXXXXXX Trypsin + Glu-C (SEQ ID NO: 65)
 61 XXXXXXXX XXXXQSTTAY MEFSSLTSED SAVYYCARYG GLEWEYAMDYW GQGTSVTVSS Trypsin (SEQ ID NO: 66)
 61 NEKXXXXXXX XXXXQSTTAY MEFSSLTSED SAVYYCARYG GLWLYAMDYW GQGTSVTVSS In-gel Trypsin (SEQ ID NO: 67)
 61 NEKXXXFKATL TSDKQSTTAY MEFSSLTSED SAVYYCARYG GLWLYAMDYW GQGTSVTVSS Glu-C (SEQ ID NO: 68)
 61 NEKXXXXXXX XXXXXXXXXX XXXXXXXXXX XXXXXXXXXX XXXXXXXXXX XXXXXXXXXX Chymotrypsin (SEQ ID NO: 69)
 61 NEKXXXXXXX XXXXXXXXXX XXXXXXXXXX XXXXXXXXXX XXXXXXXXXX XXXXXXXXXX Thermolysin (SEQ ID NO: 70)
 61 NEKFXXXXXX XXXXXXXXXX XXXXXLTSED SAVYYCARYG GLWX XXXXXXXXXX Subtilin (SEQ ID NO: 71)
 61 XXXXXXXXXX XXXXXXXXXX MEFSSLTSED SAVYYCARYG GLWLYAMDYW GQGTSVTVSS

Fig. 3B

```
                              10                  20                a      30
(SEQ ID NO: 1)
QBEND/10 V_L         Q L V L T Q S S - A S F S L G A S A K L T C T L S S Q H R T F T I E
(SEQ ID NO: 5)
IGLV4-69*01/J1*01    Q L V L T Q S P S - A S A S L G A S V K L T C T L S S G H S S Y A I A a  b                        c  d              60
(SEQ ID NO: 1)
QBEND/10 V_L         W Y Q Q Q P E K P P K Y V M E L R K D G S H S T G D G I P D R F S G S
(SEQ ID NO: 5)
IGLV4-69*01/J1*01    W H Q Q Q P E K G P R Y L M K L N S D G S H S K G D G I P D R F S G S 70                  80                      90
(SEQ ID NO: 1)
QBEND/10 V_L         S S G A D R Y L S I S N I Q P E D E A I Y I C G V G N T
(SEQ ID NO: 5)
IGLV4-69*01/J1*01    S S G A E R Y L T I S S L Q S E D E A D Y Y C Q T W G T a  b  c  d
(SEQ ID NO: 1)
QBEND/10 V_L         T K E Q F V Y V
(SEQ ID NO: 5)
IGLV4-69*01/J1*01    G T - - - Y V a
(SEQ ID NO: 1)
QBEND/10 V_L         F G G G T K V T V L
(SEQ ID NO: 5)
IGLV4-69*01/J1*01    F G T G T K V T V L
```

Fig. 5A (SEQ ID NO: 2)
QBEND/10 V_H                Q V Q L E Q S G P E L V K P G A S V K M S C K A S [ G Y T F T S Y V I H ]
(SEQ ID NO: 8)
IGHV1-3*01/J4*01            Q V Q L V Q S G A E V K K P G A S V K V S C K A S [ G Y T F T S Y A M H ]

(SEQ ID NO: 2)
QBEND/10 V_H                W V K Q K P G Q G L E W L G [ Y T N P Y N D V T K Y N E K F K F ]
(SEQ ID NO: 8)
IGHV1-3*01/J4*01            W V R Q A P G Q R L E W M G [ W I N A G N G N T K Y S Q K F Q G ]

(SEQ ID NO: 2)
QBEND/10 V_H                K A T L T S D K Q S T T A Y M E F S S L T S E D S A V Y Y C A R
(SEQ ID NO: 8)
IGHV1-3*01/J4*01            R V T I T R D T S A S T A Y M E L S S L R S E D T A V Y Y C A R (SEQ ID NO: 2)
QBEND/10 V_H                [ Y G G L W L Y A M D Y ] W G Q G T S V T V S S
(SEQ ID NO: 8)
IGHV1-3*01/J4*01            [ - - - - - Y F D Y ] W G Q G T L V T V S S

Fig. 5B

SEQUENCE LISTING

<160> NUMBER OF SEQ ID NOS: 77

<210> SEQ ID NO 1
<211> LENGTH: 115
<212> TYPE: PRT
<213> ORGANISM: Artificial Sequence
<220> FEATURE:
<223> OTHER INFORMATION: Light chain variable region of mouse QBEND/10

<400> SEQUENCE: 1

```
Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Trp Tyr Gln Gln Pro Leu Lys Pro Pro Lys Tyr Val Met
        35                  40                  45

Glu Leu Arg Lys Asp Gly Ser His Ser Thr Gly Asp Gly Ile Pro Asp
50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Gly Thr Lys Val
            100                 105                 110

Thr Val Leu
        115
```

<210> SEQ ID NO 2
<211> LENGTH: 120
<212> TYPE: PRT
<213> ORGANISM: Artificial Sequence
<220> FEATURE:
<223> OTHER INFORMATION: Heavy chain variable region of mouse QBEND/10

<400> SEQUENCE: 2

```
Gln Val Gln Leu Glu Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Leu
        35                  40                  45

Gly Tyr Thr Asn Pro Tyr Asn Asp Val Thr Lys Tyr Asn Glu Lys Phe
50                  55                  60

Lys Phe Lys Ala Thr Leu Thr Ser Asp Lys Gln Ser Thr Thr Ala Tyr
65                  70                  75                  80

Met Glu Phe Ser Ser Leu Thr Ser Glu Asp Ser Ala Val Tyr Tyr Cys
                85                  90                  95

Ala Arg Tyr Gly Gly Leu Trp Leu Tyr Ala Met Asp Tyr Trp Gly Gln
            100                 105                 110

Gly Thr Ser Val Thr Val Ser Ser
        115                 120
```

<210> SEQ ID NO 3
<211> LENGTH: 101
<212> TYPE: PRT
<213> ORGANISM: Homo sapiens

<400> SEQUENCE: 3

Gln Leu Val Leu Thr Gln Ser Pro Ser Ala Ser Ala Ser Leu Gly Ala

-continued

```
                1               5                  10                  15
Ser Val Lys Leu Thr Cys Thr Leu Ser Ser Gly His Ser Ser Tyr Ala
                    20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                    85                  90                  95

Thr Gly Ile Tyr Val
            100
```

<210> SEQ ID NO 4
<211> LENGTH: 10
<212> TYPE: PRT
<213> ORGANISM: Homo sapiens

<400> SEQUENCE: 4

```
Phe Gly Thr Gly Thr Lys Val Thr Val Leu
1               5                  10
```

<210> SEQ ID NO 5
<211> LENGTH: 111
<212> TYPE: PRT
<213> ORGANISM: Homo sapiens

<400> SEQUENCE: 5

```
Gln Leu Val Leu Thr Gln Ser Pro Ser Ala Ser Ala Ser Leu Gly Ala
1               5                  10                  15

Ser Val Lys Leu Thr Cys Thr Leu Ser Ser Gly His Ser Ser Tyr Ala
                    20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                    85                  90                  95

Thr Gly Ile Tyr Val Phe Gly Thr Gly Thr Lys Val Thr Val Leu
            100                 105                 110
```

<210> SEQ ID NO 6
<211> LENGTH: 102
<212> TYPE: PRT
<213> ORGANISM: Homo sapiens

<400> SEQUENCE: 6

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                    20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60
```

```
Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Asp Tyr
            100
```

<210> SEQ ID NO 7
<211> LENGTH: 11
<212> TYPE: PRT
<213> ORGANISM: Homo sapiens

<400> SEQUENCE: 7

```
Trp Gly Gln Gly Thr Leu Val Thr Val Ser Ser
 1               5                  10
```

<210> SEQ ID NO 8
<211> LENGTH: 113
<212> TYPE: PRT
<213> ORGANISM: Homo sapiens

<400> SEQUENCE: 8

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Asp Tyr Trp Gly Gln Gly Thr Leu Val Thr Val Ser
            100                 105                 110

Ser
```

<210> SEQ ID NO 9
<211> LENGTH: 115
<212> TYPE: PRT
<213> ORGANISM: Artificial Sequence
<220> FEATURE:
<223> OTHER INFORMATION: Light chain variable region of humanized
      QBEND/10

<400> SEQUENCE: 9

```
Gln Leu Val Leu Thr Gln Ser Pro Ser Ala Ser Phe Ser Leu Gly Ala
 1               5                  10                  15

Ser Ala Lys Leu Thr Cys Thr Leu Ser Ser Gln His Arg Thr Phe Thr
                 20                  25                  30

Ile Glu Trp Tyr Gln Gln Gln Pro Glu Lys Pro Pro Lys Tyr Val Met
             35                  40                  45

Glu Leu Arg Lys Asp Gly Ser His Ser Lys Gly Asp Gly Ile Pro Asp
 50                  55                  60

Arg Phe Ser Gly Ser Ser Ser Gly Ala Asp Arg Tyr Leu Ser Ile Ser
 65                  70                  75                  80

Ser Ile Gln Pro Glu Asp Glu Ala Ile Tyr Ile Cys Gly Val Gly Asn
```

```
                85                  90                  95
Thr Ile Lys Glu Gln Phe Val Tyr Val Phe Gly Thr Gly Thr Lys Val
            100                 105                 110

Thr Val Leu
        115

<210> SEQ ID NO 10
<211> LENGTH: 120
<212> TYPE: PRT
<213> ORGANISM: Artificial Sequence
<220> FEATURE:
<223> OTHER INFORMATION: Heavy chain variable region of humanized
      QBEND/10

<400> SEQUENCE: 10

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Leu
        35                  40                  45

Gly Tyr Thr Asn Pro Tyr Asn Asp Val Thr Lys Tyr Asn Glu Lys Phe
    50                  55                  60

Lys Phe Lys Ala Thr Leu Thr Ser Asp Thr Ser Ser Thr Thr Ala Tyr
65                  70                  75                  80

Met Glu Phe Ser Ser Leu Thr Ser Glu Asp Ser Ala Val Tyr Tyr Cys
                85                  90                  95

Ala Arg Tyr Gly Gly Leu Trp Leu Tyr Ala Met Asp Tyr Trp Gly Gln
            100                 105                 110

Gly Thr Ser Val Thr Val Ser Ser
        115                 120

<210> SEQ ID NO 11
<211> LENGTH: 345
<212> TYPE: DNA
<213> ORGANISM: Artificial Sequence
<220> FEATURE:
<223> OTHER INFORMATION: Light chain variable region of mouse QBEND/10

<400> SEQUENCE: 11
cagctcgtcc tcactcagtc ttcctcagcc tccttttccc tcggtgcctc cgccaaactc      60
acttgtactc tcagcagcca gcatagaact ttcactatcg agtggtatca gcagcagcct     120
ctgaagcccc ctaaatatgt gatggaactc cggaaggacg gaagtcactc aaccggtgac     180
ggcattccag ataggttttc tggtagctcc tctggggccg acagatacct gagcatctcc     240
aacattcagc ccgaggatga agctatctat atttgcggag tcggaatac catcaaagag      300 cagttcgtgt acgtctttgg cggagggacc aaggtgacag tcctc                     345

<210> SEQ ID NO 12
<211> LENGTH: 360
<212> TYPE: DNA
<213> ORGANISM: Artificial Sequence
<220> FEATURE:
<223> OTHER INFORMATION: Heavy chain variable region of mouse QBEND/10

<400> SEQUENCE: 12
caggtccagc tcgaacagtc aggtccagaa ctcgtcaaac caggtgcctc agtcaagatg      60
tcatgcaaag caagcggcta cacattcact agttacgtga tccactgggt caagcagaaa    120
```

```
cctggccagg gtctggagtg gctcggctac accaacccct tacaacgacgt gacaaagtac      180 aacgaaaagt tcaagttcaa ggcaactctg acctccgata agcagtctac cacagcctac      240
atggagttca gctccctcac ctcagaagac agcgccgtct actattgcgc tagatatggc      300
ggactgtggc tctacgctat ggattattgg ggccagggaa catccgtgac tgtctctagt      360

<210> SEQ ID NO 13
<211> LENGTH: 345
<212> TYPE: DNA
<213> ORGANISM: Artificial Sequence
<220> FEATURE:
<223> OTHER INFORMATION: Light chain variable region of humanized
      QBEND/10

<400> SEQUENCE: 13
cagctcgtcc tcactcagtc tccctcagcc tccttttccc tcggtgcctc cgccaaactc       60
acttgtactc tcagcagcca gcatagaact ttcactatcg agtggtatca gcagcagcct      120
gagaagcccc ctaaatatgt gatggaactc cggaaggacg gaagtcactc aaagggtgac      180
ggcattccag ataggttttc tggtagctcc tctggggccg acagatacct gagcatctcc      240
agcattcagc ccgaggatga agctatctat atttgcggag tcgggaatac catcaaagag      300
cagttcgtgt acgtctttgg cacagggacc aaggtgacag tcctc                     345

<210> SEQ ID NO 14
<211> LENGTH: 360
<212> TYPE: DNA
<213> ORGANISM: Artificial Sequence
<220> FEATURE:
<223> OTHER INFORMATION: Heavy chain variable region of humanized
      QBEND/10

<400> SEQUENCE: 14
caggtccagc tcgtacagtc aggtgcagaa ctcgtcaaac caggtgcctc agtcaagatg       60
tcatgcaaag caagcggcta cacattcact agttacgtga tccactgggt caagcagaaa      120
cctggccagg gtctggagtg gctcggctac accaacccct tacaacgacgt gacaaagtac     180 aacgaaaagt tcaagttcaa ggcaactctg acctccgata cgtcgtctac cacagcctac      240
atggagttca gctccctcac ctcagaagac agcgccgtct actattgcgc tagatatggc      300
ggactgtggc tctacgctat ggattattgg ggccagggaa catccgtgac tgtctctagt      360

<210> SEQ ID NO 15
<211> LENGTH: 19
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 15

Gln Leu Val Leu Thr Gln Ser Ser Ser Ala Ser Phe Ser Leu Gly Ala
1               5                   10                  15

Ser Ala Lys

<210> SEQ ID NO 16
<211> LENGTH: 10
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion0
```

```
<400> SEQUENCE: 16

Leu Thr Cys Thr Leu Ser Ser Gln His Arg
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 17

Thr Phe Thr Ile Glu Trp Tyr Gln Gln Gln Pro Leu Lys Pro Pro Lys
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 18

Tyr Val Met Glu Leu Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 19

Asp Gly Ser His Ser Thr Gly Asp Gly Ile Pro Asp Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 20

Phe Ser Gly Ser Ser Ser Gly Ala Asp Arg
1               5                   10

<210> SEQ ID NO 21
<211> LENGTH: 24
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 21

Tyr Leu Ser Ile Ser Asn Ile Gln Pro Glu Asp Glu Ala Ile Tyr Ile
1               5                   10                  15

Cys Gly Val Gly Asn Thr Ile Lys
            20
```

<210> SEQ ID NO 22
<211> LENGTH: 12
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 22

Glu Gln Phe Val Tyr Val Phe Gly Gly Gly Thr Lys
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 23

Val Thr Val Leu Gly Gln Pro Lys
1               5

<210> SEQ ID NO 24
<211> LENGTH: 16
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 24

Ser Thr Pro Thr Leu Thr Val Phe Pro Pro Ser Ser Glu Glu Leu Lys
1               5                   10                  15

<210> SEQ ID NO 25
<211> LENGTH: 20
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 25

Ala Thr Leu Val Cys Leu Ile Ser Asn Phe Ser Pro Ser Gly Val Thr
1               5                   10                  15

Val Ala Trp Lys
            20

<210> SEQ ID NO 26
<211> LENGTH: 17
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 26

Ala Asn Gly Thr Pro Ile Thr Gln Gly Val Asp Thr Ser Asn Pro Thr
1               5                   10                  15

Lys

<210> SEQ ID NO 27
<211> LENGTH: 4
<212> TYPE: PRT
<213> ORGANISM: Artificial Sequence -continued

```
<220> FEATURE:
<223> OTHER INFORMATION: Theoretical peptide fragment of mouse QBEND/10
      light chain obtained by trypsin digestion

<400> SEQUENCE: 27

Glu Gly Asn Lys
1

<210> SEQ ID NO 28
<211> LENGTH: 15
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 28

Phe Met Ala Ser Ser Phe Leu His Leu Thr Ser Asp Gln Trp Arg
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 29

Ser His Asn Ser Phe Thr Cys Gln Val Thr His Glu Gly Asp Thr Val
1               5                   10                  15

Glu Lys

<210> SEQ ID NO 30
<211> LENGTH: 8
<212> TYPE: PRT
<213> ORGANISM: Artificial Sequence
<220> FEATURE:
<223> OTHER INFORMATION: Theoretical peptide fragment of mouse QBEND/10
      light chain obtained by trypsin digestion

<400> SEQUENCE: 30

Ser Leu Ser Pro Ala Glu Cys Leu
1               5

<210> SEQ ID NO 31
<211> LENGTH: 19
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 31

Gln Val Gln Leu Glu Gln Ser Gly Pro Glu Leu Val Lys Pro Gly Ala
1               5                   10                  15

Ser Val Lys

<210> SEQ ID NO 32
<211> LENGTH: 4
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 32
```

```
Met Ser Cys Lys
1

<210> SEQ ID NO 33
<211> LENGTH: 15
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 33

Ala Ser Gly Tyr Thr Phe Thr Ser Tyr Val Ile His Trp Val Lys
1               5                   10                  15

<210> SEQ ID NO 34
<211> LENGTH: 21
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 34

Gln Lys Pro Gly Gln Gly Leu Glu Trp Leu Gly Tyr Thr Asn Pro Tyr
1               5                   10                  15

Asn Asp Val Thr Lys
            20

<210> SEQ ID NO 35
<211> LENGTH: 4
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 35

Tyr Asn Glu Lys
1

<210> SEQ ID NO 36
<211> LENGTH: 7
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 36

Ala Thr Leu Thr Ser Asp Lys
1               5

<210> SEQ ID NO 37
<211> LENGTH: 24
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 37

Gln Ser Thr Thr Ala Tyr Met Glu Phe Ser Ser Leu Thr Ser Glu Asp
1               5                   10                  15

Ser Ala Val Tyr Tyr Cys Ala Arg
            20
```

<210> SEQ ID NO 38
<211> LENGTH: 24
<212> TYPE: PRT
<213> ORGANISM: Artificial Sequence
<220> FEATURE:
<223> OTHER INFORMATION: Theoretical peptide fragment of mouse QBEND/10 heavy chain obtained by trypsin digestion

<400> SEQUENCE: 38

Tyr Gly Gly Leu Trp Leu Tyr Ala Met Asp Tyr Trp Gly Gln Gly Thr
1               5                   10                  15

Ser Val Thr Val Ser Ser Ala Lys
            20

<210> SEQ ID NO 39
<211> LENGTH: 28
<212> TYPE: PRT
<213> ORGANISM: Artificial Sequence
<220> FEATURE:
<223> OTHER INFORMATION: Theoretical peptide fragment of mouse QBEND/10 heavy chain obtained by trypsin digestion

<400> SEQUENCE: 39

Thr Thr Pro Pro Ser Val Tyr Pro Leu Ala Pro Gly Ser Ala Ala Gln
1               5                   10                  15

Thr Asn Ser Met Val Thr Leu Gly Cys Leu Val Lys
            20                  25

<210> SEQ ID NO 40
<211> LENGTH: 62
<212> TYPE: PRT
<213> ORGANISM: Artificial Sequence
<220> FEATURE:
<223> OTHER INFORMATION: Theoretical peptide fragment of mouse QBEND/10 heavy chain obtained by trypsin digestion

<400> SEQUENCE: 40

Gly Tyr Phe Pro Glu Pro Val Thr Val Thr Trp Asn Ser Gly Ser Leu
1               5                   10                  15

Ser Ser Gly Val His Thr Phe Pro Ala Val Leu Gln Ser Asp Leu Tyr
            20                  25                  30

Thr Leu Ser Ser Ser Val Thr Val Pro Ser Ser Thr Trp Pro Ser Glu
        35                  40                  45

Thr Val Thr Cys Asn Val Ala His Pro Ala Ser Ser Thr Lys
    50                  55                  60

<210> SEQ ID NO 41
<211> LENGTH: 4
<212> TYPE: PRT
<213> ORGANISM: Artificial Sequence
<220> FEATURE:
<223> OTHER INFORMATION: Theoretical peptide fragment of mouse QBEND/10 heavy chain obtained by trypsin digestion

<400> SEQUENCE: 41

Ile Val Pro Arg
1

<210> SEQ ID NO 42
<211> LENGTH: 25
<212> TYPE: PRT
<213> ORGANISM: Artificial Sequence
<220> FEATURE:
<223> OTHER INFORMATION: Theoretical peptide fragment of mouse QBEND/10

-continued heavy chain obtained by trypsin digestion

<400> SEQUENCE: 42

Asp Cys Gly Cys Lys Pro Cys Ile Cys Thr Val Pro Glu Val Ser Ser
1               5                   10                  15

Val Phe Ile Phe Pro Pro Lys Pro Lys
            20                  25

<210> SEQ ID NO 43
<211> LENGTH: 10
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 43

Asp Val Leu Thr Ile Thr Leu Thr Pro Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 44

Val Thr Cys Val Val Val Asp Ile Ser Lys
1               5                   10

<210> SEQ ID NO 45
<211> LENGTH: 24
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 45

Asp Asp Pro Glu Val Gln Phe Ser Trp Phe Val Asp Asp Val Glu Val
1               5                   10                  15

His Thr Ala Gln Thr Gln Pro Arg
            20

<210> SEQ ID NO 46
<211> LENGTH: 9
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 46

Glu Glu Gln Phe Asn Ser Thr Phe Arg
1               5

<210> SEQ ID NO 47
<211> LENGTH: 16
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 47

```
Ser Val Ser Glu Leu Pro Ile Met His Gln Asp Trp Leu Asn Gly Lys
1               5                   10                  15
```

<210> SEQ ID NO 48
<211> LENGTH: 12
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 48

```
Val Asn Ser Ala Ala Phe Pro Ala Pro Ile Glu Lys
1               5                   10
```

<210> SEQ ID NO 49
<211> LENGTH: 4
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 49

```
Thr Ile Ser Lys
1
```

<210> SEQ ID NO 50
<211> LENGTH: 4
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 50

```
Gly Arg Pro Lys
1
```

<210> SEQ ID NO 51
<211> LENGTH: 11
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 51

```
Ala Pro Gln Val Tyr Thr Ile Pro Pro Pro Lys
1               5                   10
```

<210> SEQ ID NO 52
<211> LENGTH: 5
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 52

```
Glu Gln Met Ala Lys
1               5
```

<210> SEQ ID NO 53
<211> LENGTH: 30
<212> TYPE: PRT
<213> ORGANISM: Artificial Sequence

```
<220> FEATURE:
<223> OTHER INFORMATION: Theoretical peptide fragment of mouse QBEND/10
      heavy chain obtained by trypsin digestion

<400> SEQUENCE: 53

Val Ser Leu Thr Cys Met Ile Thr Asp Phe Phe Pro Glu Asp Ile Thr
1               5                   10                  15

Val Glu Trp Gln Trp Asn Ala Gln Pro Ala Glu Asn Tyr Lys
            20                  25                  30

<210> SEQ ID NO 54
<211> LENGTH: 17
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 54

Asn Thr Gln Pro Ile Met Asp Thr Asp Gly Ser Tyr Phe Val Tyr Ser
1               5                   10                  15

Lys

<210> SEQ ID NO 55
<211> LENGTH: 5
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 55

Leu Asn Val Gln Lys
1               5

<210> SEQ ID NO 56
<211> LENGTH: 25
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 56

Ser Asn Trp Glu Ala Gly Asn Thr Phe Thr Cys Ser Val Leu His Glu
1               5                   10                  15

Gly Leu His Asn His His Thr Glu Lys
            20                  25

<210> SEQ ID NO 57
<211> LENGTH: 8
<212> TYPE: PRT
<213> ORGANISM: Artificial Sequence
<220> FEATURE:
<223> OTHER INFORMATION: Theoretical peptide fragment of mouse QBEND/10
      heavy chain obtained by trypsin digestion

<400> SEQUENCE: 57

Ser Leu Ser His Ser Pro Gly Lys
1               5

<210> SEQ ID NO 58
<211> LENGTH: 120
<212> TYPE: PRT
<213> ORGANISM: Artificial Sequence
<220> FEATURE:
```

```
<223> OTHER INFORMATION: The identification result of the variable
      region of light chain obtained by trypsin and endopeptidase
      digestion
<220> FEATURE:
<221> NAME/KEY: misc_feature
<222> LOCATION: (46)..(52)
<223> OTHER INFORMATION: Xaa is an unknown amino acid
<220> FEATURE:
<221> NAME/KEY: misc_feature
<222> LOCATION: (66)..(75)
<223> OTHER INFORMATION: Xaa is an unknown amino acid

<400> SEQUENCE: 58

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Trp Tyr Gln Gln Pro Leu Lys Pro Pro Lys Xaa Xaa Xaa
                35                  40                  45

Xaa Xaa Xaa Xaa Asp Gly Ser His Ser Thr Gly Asp Gly Ile Pro Asp
50                          55                  60

Arg Xaa Xaa Xaa Xaa Xaa Xaa Xaa Xaa Xaa Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Thr Lys Val
            100                 105                 110

Thr Val Leu Gly Gln Pro Lys Ser
        115                 120

<210> SEQ ID NO 59
<211> LENGTH: 120
<212> TYPE: PRT
<213> ORGANISM: Artificial Sequence
<220> FEATURE:
<223> OTHER INFORMATION: The identification result of the variable
      region of light chain obtained by trypsin digestion
<220> FEATURE:
<221> NAME/KEY: misc_feature
<222> LOCATION: (112)..(119)
<223> OTHER INFORMATION: Xaa is an unknown amino acid

<400> SEQUENCE: 59

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Trp Tyr Gln Gln Pro Leu Lys Pro Pro Lys Tyr Val Met
                35                  40                  45

Glu Leu Arg Lys Asp Gly Ser His Ser Thr Gly Asp Gly Ile Pro Asp
50                          55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Thr Lys Xaa
            100                 105                 110

Xaa Xaa Xaa Xaa Xaa Xaa Xaa Ser
        115                 120

<210> SEQ ID NO 60
```

<211> LENGTH: 120
<212> TYPE: PRT
<213> ORGANISM: Artificial Sequence
<220> FEATURE:
<223> OTHER INFORMATION: The identification result of the variable
      region of light chain obtained by in-gel trypsin digestion

<400> SEQUENCE: 60

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Trp Tyr Gln Gln Pro Leu Lys Pro Pro Lys Tyr Val Met
            35                  40                  45

Glu Leu Arg Lys Asp Gly Ser His Ser Thr Gly Asp Gly Ile Pro Asp
50                      55                      60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Gly Thr Lys Val
            100                 105                 110

Thr Val Leu Gly Gln Pro Lys Ser
        115                 120

<210> SEQ ID NO 61
<211> LENGTH: 120
<212> TYPE: PRT
<213> ORGANISM: Artificial Sequence
<220> FEATURE:
<223> OTHER INFORMATION: The identification result of the variable
      region of light chain obtained by endopeptidase digestion
<220> FEATURE:
<221> NAME/KEY: misc_feature
<222> LOCATION: (35)..(85)
<223> OTHER INFORMATION: Xaa is an unknown amino acid

<400> SEQUENCE: 61

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                      55                      60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Asp Glu Ala Ile Tyr Ile Cys Gly Val Gly Asn
                85                  90                  95

Thr Ile Lys Glu Gln Phe Val Tyr Val Phe Gly Gly Gly Thr Lys Val
            100                 105                 110

Thr Val Leu Gly Gln Pro Lys Ser
        115                 120

<210> SEQ ID NO 62
<211> LENGTH: 120
<212> TYPE: PRT
<213> ORGANISM: Artificial Sequence
<220> FEATURE:
<223> OTHER INFORMATION: The identification result of the variable region of light chain obtained by chymotrypsin digestion
<220> FEATURE:
<221> NAME/KEY: misc_feature
<222> LOCATION: (25)..(36)
<223> OTHER INFORMATION: Xaa is an unknown amino acid
<220> FEATURE:
<221> NAME/KEY: misc_feature
<222> LOCATION: (105)..(120)
<223> OTHER INFORMATION: Xaa is an unknown amino acid

<400> SEQUENCE: 62

Gln Leu Val Leu Thr Gln Ser Ser Ala Ser Phe Ser Leu Gly Ala
1               5                   10                  15

Ser Ala Lys Leu Thr Cys Thr Leu Xaa Xaa Xaa Xaa Xaa Xaa Xaa
            20                  25                  30

Xaa Xaa Xaa Xaa Gln Gln Gln Pro Leu Lys Pro Pro Lys Tyr Val Met
            35                  40                  45

Glu Leu Arg Lys Asp Gly Ser His Ser Thr Gly Asp Gly Ile Pro Asp
50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Xaa Xaa Xaa Xaa Xaa Xaa Xaa
            100                 105                 110

Xaa Xaa Xaa Xaa Xaa Xaa Xaa Xaa
            115                 120

<210> SEQ ID NO 63
<211> LENGTH: 120
<212> TYPE: PRT
<213> ORGANISM: Artificial Sequence
<220> FEATURE:
<223> OTHER INFORMATION: The identification result of the variable
      region of light chain obtained by thermolysin digestion
<220> FEATURE:
<221> NAME/KEY: misc_feature
<222> LOCATION: (20)..(23)
<223> OTHER INFORMATION: Xaa is an unknown amino acid
<220> FEATURE:
<221> NAME/KEY: misc_feature
<222> LOCATION: (47)..(49)
<223> OTHER INFORMATION: Xaa is an unknown amino acid
<220> FEATURE:
<221> NAME/KEY: misc_feature
<222> LOCATION: (77)..(104)
<223> OTHER INFORMATION: Xaa is an unknown amino acid

<400> SEQUENCE: 63

Gln Leu Val Leu Thr Gln Ser Ser Ala Ser Phe Ser Leu Gly Ala
1               5                   10                  15

Ser Ala Lys Xaa Xaa Xaa Xaa Leu Ser Ser Gln His Arg Thr Phe Thr
            20                  25                  30

Ile Glu Trp Tyr Gln Gln Gln Pro Leu Lys Pro Pro Lys Tyr Xaa Xaa
            35                  40                  45

Xaa Leu Arg Lys Asp Gly Ser His Ser Thr Gly Asp Gly Ile Pro Asp
50                  55                  60

Arg Phe Ser Gly Ser Ser Ser Gly Ala Asp Arg Tyr Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Val Phe Gly Gly Thr Lys Val
            100                 105                 110

Thr Val Leu Gly Gln Pro Lys Ser
            115                 120

<210> SEQ ID NO 64
<211> LENGTH: 120
<212> TYPE: PRT
<213> ORGANISM: Artificial Sequence
<220> FEATURE:
<223> OTHER INFORMATION: The identification result of the variable
      region of light chain obtained by subtilisin digestion
<220> FEATURE:
<221> NAME/KEY: misc_feature
<222> LOCATION: (35)..(36)
<223> OTHER INFORMATION: Xaa is an unknown amino acid
<220> FEATURE:
<221> NAME/KEY: misc_feature
<222> LOCATION: (48)..(50)
<223> OTHER INFORMATION: Xaa is an unknown amino acid
<220> FEATURE:
<221> NAME/KEY: misc_feature
<222> LOCATION: (70)..(75)
<223> OTHER INFORMATION: Xaa is an unknown amino acid
<220> FEATURE:
<221> NAME/KEY: misc_feature
<222> LOCATION: (100)..(119)
<223> OTHER INFORMATION: Xaa is an unknown amino acid

<400> SEQUENCE: 64

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Arg Thr Phe Thr
            20                  25                  30

Ile Glu Xaa Xaa Gln Gln Pro Leu Lys Pro Pro Lys Tyr Val Xaa
            35                  40                  45

Xaa Xaa Arg Lys Asp Gly Ser His Ser Thr Gly Asp Gly Ile Pro Asp
50                  55                  60

Arg Phe Ser Gly Ser Xaa Xaa Xaa Xaa Xaa Xaa Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Xaa Xaa Xaa Xaa Xaa Xaa Xaa Xaa Xaa Xaa Xaa Xaa
            100                 105                 110

Xaa Xaa Xaa Xaa Xaa Xaa Xaa Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: The identification result of the variable
      region of heavy chain obtained by trypsin and endopeptidase
      digestion
<220> FEATURE:
<221> NAME/KEY: misc_feature
<222> LOCATION: (20)..(23)
<223> OTHER INFORMATION: Xaa is an unknown amino acid
<220> FEATURE:
<221> NAME/KEY: misc_feature
<222> LOCATION: (60)..(74)
<223> OTHER INFORMATION: Xaa is an unknown amino acid

<400> SEQUENCE: 65

Gln Val Gln Leu Glu Gln Ser Gly Pro Glu Leu Val Lys Pro Gly Ala
1               5                   10                  15

Ser Val Lys Xaa Xaa Xaa Xaa Ala Ser Gly Tyr Thr Phe Thr Ser Tyr

```
                    20                  25                  30
Val Ile His Trp Val Lys Gln Lys Pro Gly Gln Gly Leu Glu Trp Leu
             35                  40                  45

Gly Tyr Thr Asn Pro Tyr Asn Asp Val Thr Lys Xaa Xaa Xaa Xaa
         50                  55                  60

Xaa Xaa Xaa Xaa Xaa Xaa Xaa Xaa Xaa Gln Ser Thr Thr Ala Tyr
65                  70                  75                  80

Met Glu Phe Ser Ser Leu Thr Ser Glu Asp Ser Ala Val Tyr Tyr Cys
                 85                  90                  95

Ala Arg Tyr Gly Gly Leu Trp Leu Tyr Ala Met Asp Tyr Trp Gly Gln
            100                 105                 110

Gly Thr Ser Val Thr Val Ser Ser
            115                 120

<210> SEQ ID NO 66
<211> LENGTH: 120
<212> TYPE: PRT
<213> ORGANISM: Artificial Sequence
<220> FEATURE:
<223> OTHER INFORMATION: The identification result of the variable
      region of heavy chain obtained by trypsin digestion
<220> FEATURE:
<221> NAME/KEY: misc_feature
<222> LOCATION: (20)..(24)
<223> OTHER INFORMATION: Xaa is an unknown amino acid
<220> FEATURE:
<221> NAME/KEY: misc_feature
<222> LOCATION: (64)..(74)
<223> OTHER INFORMATION: Xaa is an unknown amino acid

<400> SEQUENCE: 66

Gln Val Gln Leu Glu Gln Ser Gly Pro Glu Leu Val Lys Pro Gly Ala
1               5                   10                  15

Ser Val Lys Xaa Xaa Xaa Xaa Xaa Ser Gly Tyr Thr Phe Thr Ser Tyr
            20                  25                  30

Val Ile His Trp Val Lys Gln Lys Pro Gly Gln Gly Leu Glu Trp Leu
             35                  40                  45

Gly Tyr Thr Asn Pro Tyr Asn Asp Val Thr Lys Tyr Asn Glu Lys Xaa
         50                  55                  60

Xaa Xaa Xaa Xaa Xaa Xaa Xaa Xaa Xaa Gln Ser Thr Thr Ala Tyr
65                  70                  75                  80

Met Glu Phe Ser Ser Leu Thr Ser Glu Asp Ser Ala Val Tyr Tyr Cys
                 85                  90                  95

Ala Arg Tyr Gly Gly Leu Trp Leu Tyr Ala Met Asp Tyr Trp Gly Gln
            100                 105                 110

Gly Thr Ser Val Thr Val Ser Ser
            115                 120

<210> SEQ ID NO 67
<211> LENGTH: 120
<212> TYPE: PRT
<213> ORGANISM: Artificial Sequence
<220> FEATURE:
<223> OTHER INFORMATION: The identification result of the variable
      region of heavy chain obtained by in-gel trypsin digestion
<220> FEATURE:
<221> NAME/KEY: misc_feature
<222> LOCATION: (64)..(65)
<223> OTHER INFORMATION: Xaa is an unknown amino acid

<400> SEQUENCE: 67

Gln Val Gln Leu Glu Gln Ser Gly Pro Glu Leu Val Lys Pro Gly Ala
```

```
                1               5                  10                  15
Ser Val Lys Met Ser Cys Lys Ala Ser Gly Tyr Thr Phe Thr Ser Tyr
                20                  25                  30

Val Ile His Trp Val Lys Gln Lys Pro Gly Gln Gly Leu Glu Trp Leu
                35                  40                  45

Gly Tyr Thr Asn Pro Tyr Asn Asp Val Thr Lys Tyr Asn Glu Lys Xaa
        50                  55                  60

Xaa Phe Lys Ala Thr Leu Thr Ser Asp Lys Gln Ser Thr Thr Ala Tyr
65                  70                  75                  80

Met Glu Phe Ser Ser Leu Thr Ser Glu Asp Ser Ala Val Tyr Tyr Cys
                85                  90                  95

Ala Arg Tyr Gly Gly Leu Trp Leu Tyr Ala Met Asp Tyr Trp Gly Gln
                100                 105                 110

Gly Thr Ser Val Thr Val Ser Ser
        115                 120
```

<210> SEQ ID NO 68
<211> LENGTH: 120
<212> TYPE: PRT
<213> ORGANISM: Artificial Sequence
<220> FEATURE:
<223> OTHER INFORMATION: The identification result of the variable
      region of heavy chain obtained by endopeptidase digestion
<220> FEATURE:
<221> NAME/KEY: misc_feature
<222> LOCATION: (1)..(46)
<223> OTHER INFORMATION: Xaa is an unknown amino acid
<220> FEATURE:
<221> NAME/KEY: misc_feature
<222> LOCATION: (63)..(120)
<223> OTHER INFORMATION: Xaa is an unknown amino acid

<400> SEQUENCE: 68

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Trp Leu
                35                  40                  45

Gly Tyr Thr Asn Pro Tyr Asn Asp Val Thr Lys Tyr Asn Glu Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa
        115                 120
```

<210> SEQ ID NO 69
<211> LENGTH: 120
<212> TYPE: PRT
<213> ORGANISM: Artificial Sequence
<220> FEATURE:
<223> OTHER INFORMATION: The identification result of the variable
      region of heavy chain obtained by chymotrypsin digestion
<220> FEATURE:
<221> NAME/KEY: misc_feature
<222> LOCATION: (1)..(50)
<223> OTHER INFORMATION: Xaa is an unknown amino acid
<220> FEATURE:

<221> NAME/KEY: misc_feature
<222> LOCATION: (65)..(120)
<223> OTHER INFORMATION: Xaa is an unknown amino acid

<400> SEQUENCE: 69

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Thr Asn Pro Tyr Asn Asp Val Thr Lys Tyr Asn Glu Lys Phe
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa
        115                 120

<210> SEQ ID NO 70
<211> LENGTH: 120
<212> TYPE: PRT
<213> ORGANISM: Artificial Sequence
<220> FEATURE:
<223> OTHER INFORMATION: The identification result of the variable
      region of heavy chain obtained by thermolysin digestion
<220> FEATURE:
<221> NAME/KEY: misc_feature
<222> LOCATION: (1)..(47)
<223> OTHER INFORMATION: Xaa is an unknown amino acid
<220> FEATURE:
<221> NAME/KEY: misc_feature
<222> LOCATION: (64)..(85)
<223> OTHER INFORMATION: Xaa is an unknown amino acid
<220> FEATURE:
<221> NAME/KEY: misc_feature
<222> LOCATION: (104)..(120)
<223> OTHER INFORMATION: Xaa is an unknown amino acid

<400> SEQUENCE: 70

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Leu
        35                  40                  45

Gly Tyr Thr Asn Pro Tyr Asn Asp Val Thr Lys Tyr Asn Glu Lys Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Leu Thr Ser Glu Asp Ser Ala Val Tyr Tyr Cys
                85                  90                  95

Ala Arg Tyr Gly Gly Leu Trp Xaa Xaa Xaa Xaa Xaa Xaa Xaa Xaa
            100                 105                 110

Xaa Xaa Xaa Xaa Xaa Xaa Xaa Xaa
        115                 120

<210> SEQ ID NO 71

-continued

```
<211> LENGTH: 120
<212> TYPE: PRT
<213> ORGANISM: Artificial Sequence
<220> FEATURE:
<223> OTHER INFORMATION: The identification result of the variable
      region of heavy chain obtained by subtilisin digestion
<220> FEATURE:
<221> NAME/KEY: misc_feature
<222> LOCATION: (1)..(5)
<223> OTHER INFORMATION: Xaa is an unknown amino acid
<220> FEATURE:
<221> NAME/KEY: misc_feature
<222> LOCATION: (18)..(23)
<223> OTHER INFORMATION: Xaa is an unknown amino acid
<220> FEATURE:
<221> NAME/KEY: misc_feature
<222> LOCATION: (39)..(74)
<223> OTHER INFORMATION: Xaa is an unknown amino acid

<400> SEQUENCE: 71

Xaa Xaa Xaa Xaa Xaa Gln Ser Gly Pro Glu Leu Val Lys Pro Gly Ala
1               5                   10                  15

Ser Xaa Xaa Xaa Xaa Xaa Xaa Ala Ser Gly Tyr Thr Phe Thr Ser Tyr
            20                  25                  30

Val Ile His Trp Val Lys Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Gln Ser Thr Thr Ala Tyr
65                  70                  75                  80

Met Glu Phe Ser Ser Leu Thr Ser Glu Asp Ser Ala Val Tyr Tyr Cys
                85                  90                  95

Ala Arg Tyr Gly Gly Leu Trp Leu Tyr Ala Met Asp Tyr Trp Gly Gln
            100                 105                 110

Gly Thr Ser Val Thr Val Ser Ser
            115                 120

<210> SEQ ID NO 72
<211> LENGTH: 12
<212> TYPE: PRT
<213> ORGANISM: Artificial Sequence
<220> FEATURE:
<223> OTHER INFORMATION: Light chain CDR1 of mouse QBEND/10

<400> SEQUENCE: 72

Thr Leu Ser Ser Gln His Arg Thr Phe Thr Ile Glu
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Light chain CDR2 of mouse QBEND/10

<400> SEQUENCE: 73

Leu Arg Lys Asp Gly Ser His
1               5

<210> SEQ ID NO 74
<211> LENGTH: 13
<212> TYPE: PRT
<213> ORGANISM: Artificial Sequence
<220> FEATURE:
<223> OTHER INFORMATION: Light chain CDR3 of mouse QBEND/10
```

```
<400> SEQUENCE: 74

Gly Val Gly Asn Thr Ile Lys Glu Gln Phe Val Tyr Val
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Heavy chain CDR1 of mouse QBEND/10

<400> SEQUENCE: 75

Gly Tyr Thr Phe Thr Ser Tyr Val Ile His
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Heavy chain CDR2 of mouse QBEND/10

<400> SEQUENCE: 76

Tyr Thr Asn Pro Tyr Asn Asp Val Thr Lys Tyr Asn Glu Lys Phe Lys
1               5                   10                  15

Phe

<210> SEQ ID NO 77
<211> LENGTH: 11
<212> TYPE: PRT
<213> ORGANISM: Artificial Sequence
<220> FEATURE:
<223> OTHER INFORMATION: Heavy chain CDR3 of mouse QBEND/10

<400> SEQUENCE: 77

Tyr Gly Gly Leu Trp Leu Tyr Ala Met Asp Tyr
1               5                   10
```

HUMANIZED MONOCLONAL ANTIBODY AND USES THEREOF

CROSS REFERENCE TO RELATED APPLICATIONS

This application claims the benefit of U.S. Provisional Application No. 62/333,339, filed May 9, 2016 and Taiwan Patent Application No. 105,143,525, filed Dec. 28, 2016. The disclosure of the application is incorporated herein by reference.

INCORPORATION BY REFERENCE OF SEQUENCE LISTING

A sequence listing submitted as a text file via EFS-Web is incorporated herein by reference. The text file containing the sequence listing is named "0965-A25187-US_Seq_Listing.txt"; its date of creation is May 8, 2017; and its size is 45,508 bytes.

TECHNICAL FIELD

The technical field relates to a humanized monoclonal antibody and uses thereof.

BACKGROUND

The surface antigen, CD34 protein, is a member of a family of single-pass transmembrane sialomucin proteins with an apparent molecular weight (Mr) of approximately 115 kD. $CD34^+$ cells are normally found in the bone marrow and umbilical cord blood, such as hematopoietic stem cells (HSCs), endothelial progenitor cells and activated endothelial cells of blood vessels. Current studies have pointed out that $CD34^+$ hematopoietic progenitor cells are a well-characterized population of stem cells, which have been used clinically to reconstitute the hematopoietic system after irradiation or chemotherapy. Otherwise, in vitro studies have demonstrated that CD34 expressed on human vascular endothelial cells (HUVECs) show the angiogenic tip cell phenotype, as well as in vivo studies have illustrated that $CD34^{-/-}$ mice exhibit abnormal vessel morphology.

QBEND/10 is a mouse monoclonal antibody (mAb) raised against CD34 and confirmed its reactivity with the class II epitope of CD34. Due to most monoclonal antibodies originate from mouse, a human anti-mouse antibody (HAMA) or a human anti-chimeric antibody (HACA) might be evoked accordingly when the murine antibodies are applied in human therapy. Hence, the murine antibodies need to be humanized for clinical application to prevent this kind of adverse immune response.

Angiogenesis is the physiological process which related to the sprouting and growth of new vessels from an existing vasculature. Angiogenesis is also the most common pathway for neo-vessel growth in malignancy, and the process is thus called tumor angiogenesis.

Therefore, there is an urgent demand to develop a novel humanized monoclonal antibody against CD34 and a specific biological agents for inhibition of angiogenesis at present.

SUMMARY

The disclosure provides a humanized monoclonal antibody, which comprises a light chain variable region and a heavy chain variable region. The light chain variable region comprises an amino acid sequence as set forth in SEQ ID NO: 1 or an amino acid sequence with at least 80% sequence identity to the sequence of SEQ ID NO: 1, and the heavy chain variable region comprises an amino acid sequence as set forth in SEQ ID NO: 2 or an amino acid sequence with at least 80% sequence identity to the sequence of SEQ ID NO: 2. In which, the amino acid sequence of SEQ ID NO: 1 and the amino acid sequence of SEQ ID NO: 2 have at least one substitute selected from a group consisting of the following: the amino acid Serine at position 8 of SEQ ID NO: 1 is substituted with Proline, the amino acid Leucine at position 41 of SEQ ID NO: 1 is substituted with Glutamic acid, the amino acid Threonine at position 58 of SEQ ID NO: 1 is substituted with Lysine, the amino acid Asparagine at position 81 of SEQ ID NO: 1 is substituted with Serine, the amino acid Glycine at position 108 of SEQ ID NO: 1 is substituted with Threonine, the amino acid Glutamine Glutamic acid at position 5 of SEQ ID NO: 2 is substituted with Valine, the amino acid Proline at position 9 of SEQ ID NO: 2 is substituted with Alanine, the amino acid Lysine at position 74 of SEQ ID NO: 2 is substituted with Threonine, and the amino acid Glutamine at position 75 of SEQ ID NO: 2 is substituted with Serine. Moreover, the humanized monoclonal antibody binds to a CD34 antigen.

The disclosure also provides a humanized monoclonal antibody, which comprises a light chain variable region and a heavy chain variable region. In which, the nucleotide sequence encoding the amino acid sequence of the light chain variable region comprises a first nucleotide sequence, and the first nucleotide sequence encodes an amino acid sequence as set forth in SEQ ID NO: 9 or an amino acid sequence with at least 80% sequence identity to the sequence of SEQ ID NO: 9, and the nucleotide sequence encoding the amino acid sequence of the heavy chain variable region comprises a second nucleotide sequence, and the second nucleotide sequence encodes an amino acid sequence as set forth in SEQ ID NO: 10 or an amino acid sequence with at least 80% sequence identity to the sequence of SEQ ID NO: 10. Moreover, the humanized monoclonal antibody binds to a CD34 antigen.

In addition, the disclosure still provides a humanized monoclonal antibody, which comprises a light chain variable region and a heavy chain variable region. In which, the nucleotide sequence encoding the light chain variable region comprises a first nucleotide sequence as set forth in SEQ ID NO: 13 or a first nucleotide sequence with at least 80% sequence identity to the sequence of SEQ ID NO: 13, and the nucleotide sequence encoding the heavy chain variable region comprises a second nucleotide sequence as set forth in SEQ ID NO: 14 or a second nucleotide sequence with at least 80% sequence identity to the sequence of SEQ ID NO: 14. Moreover, the humanized monoclonal antibody binds to a CD34 antigen.

Further, the disclosure provides a method for treating angiogenesis and/or angiogenesis-related diseases, including administering an effective amount of the above-mentioned humanized monoclonal antibody to a subject in need thereof to treat angiogenesis and/or angiogenesis-related diseases.

A detailed description is given in the following embodiments with reference to the accompanying drawings.

BRIEF DESCRIPTION OF THE DRAWINGS

The embodiments can be more fully understood by reading the subsequent detailed description and examples with references made to the accompanying drawings, wherein:

FIGS. 3A and 3B show the multiple enzyme digestion and in-gel digestion sequence alignment for QBEND/10 light chain variable region (A) and heavy chain variable region (B).

FIGS. 5A and 5B show the sequence alignment of murine QBEND/10 with corresponding human germline sequence. QBEND/10 light chain variable region (A) and heavy chain variable region (B) are sequence aligned to the most homologous human germline genes IGHV1-3*01/J4*01 and IGLV4-69*01/J1*01, respectively. In which, conserved surface residues are marked with empty boxes, and non-conserved surface residues are highlighted in shaded boxes. CDRs (within brackets) are unchanged. Residue numbers are coded according to Kabat et al. (Kabat E A, Wu, T. T., Bilofsky, H., Reid-Miller, M., Perry, H. Sequence of Proteins of Immunological Interest. National Institutes of Health, Bethesda, 1983)

DETAILED DESCRIPTION

Figure 1:
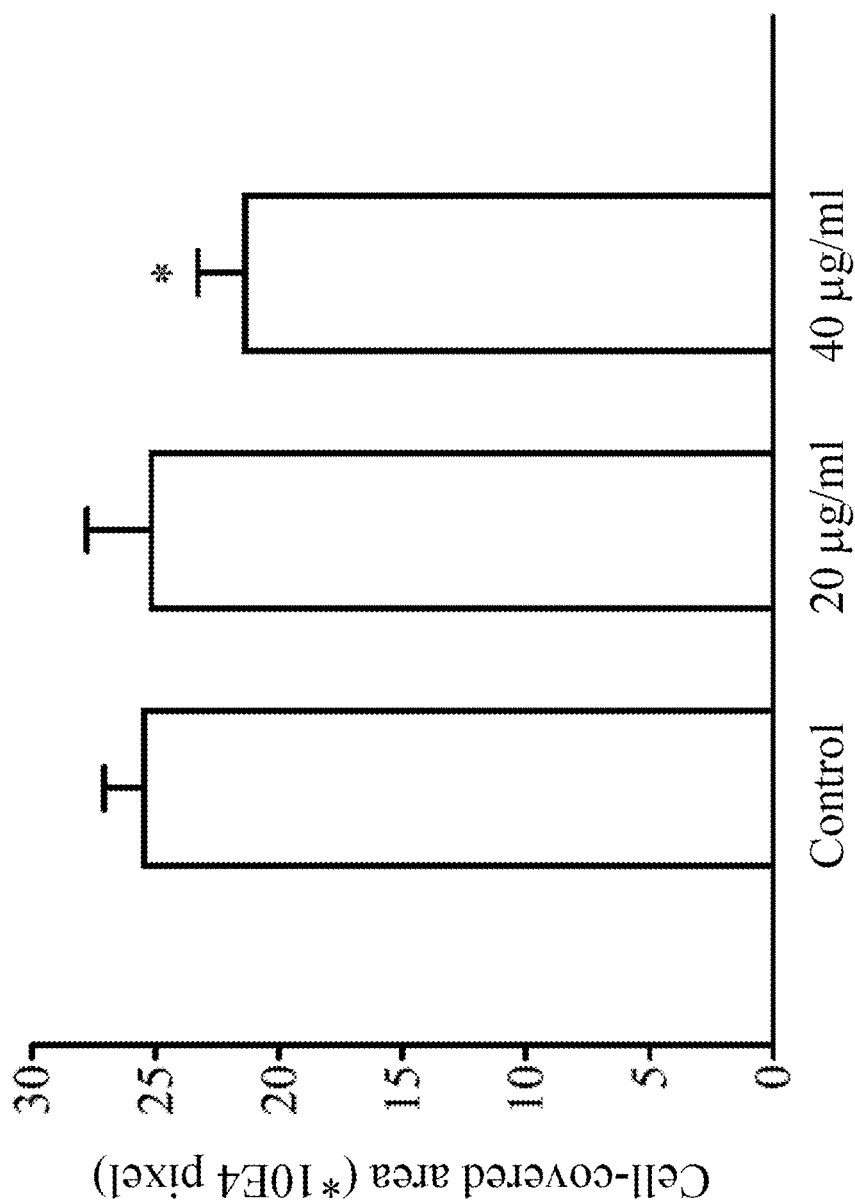
FIG. 1 shows the mouse QBEND/10 impaired tube formation of human umbilical vascular endothelial cells.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to embodiments of the disclosure, a humanized monoclonal antibody is provided. In which, the humanized monoclonal antibody binds to a CD34 antigen and the CD34 antigen can be human CD34 antigen. The foregoing humanized monoclonal antibody can comprise a light chain variable region and a heavy chain variable region. In one embodiment, the humanized monoclonal antibody can be an immunoglobulin G (IgG) antibody, which may include a light chain variable region, a heavy chain variable region, and a human immunoglobulin G conserved region.

In one embodiment, both the amino acid sequence of the light chain variable region and the amino acid sequence of the heavy chain variable region of the humanized monoclonal antibody can be obtained by performing variable domain resurfacing of non-human monoclonal antibodies bound to CD34. The steps of foregoing variable domain resurfacing in the present disclosure may be as follows, but it is not limited thereto.

First, an amino acid sequence of light chain variable region and an amino acid sequence of heavy chain variable region of the non-human monoclonal antibody bound to CD34 are provided. In one embodiment, the non-human monoclonal antibody bound to CD34 can comprise a murine monoclonal antibody. In which, the light chain variable region of the murine monoclonal antibody can comprise an amino acid sequence as set forth in SEQ ID NO: 1 or an amino acid sequence with at least 80% sequence identity to the sequence of SEQ ID NO: 1, and the heavy chain variable region can comprise an amino acid sequence as set forth in SEQ ID NO: 2 or an amino acid sequence with at least 80% sequence identity to the sequence of SEQ ID NO: 2. Moreover, the murine monoclonal antibody can be commercially available antibodies, such as QBEND/10.

In the disclosure, The term "at least 80% sequence identity" means that a sequence has a sequence identity of greater than or equal to 80%, such as 80%, 85%, 90%, 92%, 95%, 99%, 99.9%, or 100% sequence identity, but it is not limited thereto.

Next, based on the amino acid sequences of the light and heavy chains of the non-humanized monoclonal antibody bound to CD34 antigen, the molecular modeling structure of the light and heavy chains of the above-mentioned non-human monoclonal antibody was established, as well as the surface accessible residues were also determined. In one embodiment, the molecular modeling structure can be performed by the current known simulation programs or software, such as Prediction of ImmunoGlobulin Structure (PIGS), but it is not limited thereto.

Thereafter, the human sequence with the highest identity to the variable region amino acid sequence of non-human monoclonal antibody bound to CD34 were searched and the substitutable residues thereof were determined by comparison of the above-mentioned two sequences. Moreover, the substitutable residues of variable region amino acid sequence of the non-human monoclonal antibody bound to CD34 can be substituted with the amino acid residues corresponding to the position of the aforementioned residues of the human sequence. Then, the amino acid sequences of the light and heavy chain variable regions of the humanized monoclonal antibody bound to CD34 can be obtained and provided.

In one embodiment, the above-mentioned light chain variable region of the non-human monoclonal antibody bound to CD34 can comprise an amino acid sequence as set forth in SEQ ID NO: 1 or an amino acid sequence with at least 80% sequence identity to the sequence of SEQ ID NO: 1, and the heavy chain variable region can comprise an amino acid sequence as set forth in SEQ ID NO: 2 or an amino acid sequence with at least 80% sequence identity to the sequence of SEQ ID NO: 2. In addition, the human sequence with the highest identity to the $V_L$ amino acid sequence of the non-human monoclonal antibody is the light chain variable region sequence (SEQ ID NO: 5), which is composed of human germline V region from IGLV4-69*01 group (SEQ ID NO: 3) and human common sequence J region from IGLJ1*01 (SEQ ID NO: 4). Moreover, the human sequence with the highest identity to the $V_H$ amino acid sequence of the non-human monoclonal antibody is the heavy chain variable region sequence (SEQ ID NO: 8), which is composed of human germline V region from IGHV1-3*01 group (SEQ ID NO: 6) and human common sequence J region from IGHJ4*01 (SEQ ID NO: 7).

In one embodiment, the amino acid sequences of the light and heavy chain variable regions of the foregoing non-human monoclonal antibody can comprise at least one substitution as follows: the amino acid at position 8 of the $V_L$ amino acid sequence of the foregoing non-human monoclonal antibody is substituted with Proline, the amino acid at position 41 of the $V_L$ amino acid sequence of the foregoing non-human monoclonal antibody is substituted with Glutamic acid, the amino acid at position 58 of the $V_L$ amino acid sequence of the foregoing non-human monoclonal antibody is substituted with Lysine, the amino acid at position 81 of the $V_L$ amino acid sequence of the foregoing non-human monoclonal antibody is substituted with Serine, the amino acid at position 108 of the $V_L$ amino acid sequence of the foregoing non-human monoclonal antibody is substituted with Threonine, the amino acid at position 5 of the $V_H$ amino acid sequence of the foregoing non-human monoclonal antibody is substituted with Valine, the amino acid at position 9 of the $V_H$ amino acid sequence of the foregoing non-human monoclonal antibody is substituted with Alanine, the amino acid at position 74 of the $V_H$ amino acid sequence of the foregoing non-human monoclonal antibody is substituted with Threonine, and the amino acid at position 75 of the $V_H$ amino acid sequence of the foregoing non-human monoclonal antibody is substituted with Serine.

Hence, the humanized monoclonal antibody bound to CD34 obtained from the foregoing embodiment can comprise a light chain variable region and a heavy chain variable region. In which, the light chain variable region can comprise an amino acid sequence as set forth in SEQ ID NO: 1 or an amino acid sequence with at least 80% sequence identity to the sequence of SEQ ID NO: 1, and the heavy chain variable region can comprise an amino acid sequence as set forth in SEQ ID NO: 2 or an amino acid sequence with at least 80% sequence identity to the sequence of SEQ ID NO: 2.

Further, the amino acid sequences of the foregoing light and heavy chain variable regions can comprise at least one substitution as follows: the amino acid at position 8 of the amino acid sequence of the foregoing $V_L$ is substituted with Proline, the amino acid at position 41 of the amino acid sequence of the foregoing $V_L$ is substituted with Glutamic acid, the amino acid at position 58 of the amino acid sequence of the foregoing $V_L$ is substituted with Lysine, the amino acid at position 81 of the amino acid sequence of the foregoing $V_L$ is substituted with Serine, the amino acid at position 108 of the amino acid sequence of the foregoing $V_L$ is substituted with Threonine, the amino acid at position 5 of the amino acid sequence of the foregoing $V_H$ is substituted with Valine, the amino acid at position 9 of the amino acid sequence of the foregoing $V_H$ is substituted with Alanine, the amino acid at position 74 of the amino acid sequence of the foregoing $V_H$ is substituted with Threonine, and the amino acid at position 75 of the amino acid sequence of the foregoing $V_H$ is substituted with Serine.

In another embodiment, the above-mentioned light chain variable region of the non-human monoclonal antibody bound to CD34 can comprise an amino acid sequence as set forth in SEQ ID NO: 1, and the heavy chain variable region comprising an amino acid sequence as set forth in SEQ ID NO: 2. In addition, the human sequence with the highest identity to the $V_L$ amino acid sequence of the non-human monoclonal antibody is the light chain variable region sequence (SEQ ID NO: 5), which is composed of human germline V region from IGLV4-69*01 group (SEQ ID NO: 3) and human common sequence J region from IGLJ1*01 (SEQ ID NO: 4). Moreover, the human sequence with the highest identity to the $V_H$ amino acid sequence of the non-human monoclonal antibody is the heavy chain variable region sequence (SEQ ID NO: 8), which is composed of human germline V region from IGHV1-3*01 group (SEQ ID NO: 6) and human common sequence J region from IGHJ4*01 (SEQ ID NO: 7).

In one embodiment, the amino acid sequences of the light and heavy chain variable regions of the foregoing non-human monoclonal antibody bound to CD34 can comprise at least one substitute as follows: the amino acid Serine at position 8 of SEQ ID NO: 1 is substituted with Proline (Ser8Pro), the amino acid Leucine at position 41 of SEQ ID NO: 1 is substituted with Glutamic acid (Leu41Glu), the amino acid Threonine at position 58 of SEQ ID NO: 1 is substituted with Lysine (Thr58Lys), the amino acid Asparagine at position 81 of SEQ ID NO: 1 is substituted with Serine (Asn81Ser), the amino acid Glycine at position 108 of SEQ ID NO: 1 is substituted with Threonine (Gly108Thr), the amino acid Glutamic acid at position 5 of SEQ ID NO: 2 is substituted with Valine (Glu5Val), the amino acid Proline at position 9 of SEQ ID NO: 2 is substituted with Alanine (Pro9Ala), the amino acid Lysine at position 74 of SEQ ID NO: 2 is substituted with Threonine (Lys74Thr), and the amino acid Glutamine at position 75 of SEQ ID NO: 2 is substituted with Serine (Gln75Ser).

Hence, the humanized monoclonal antibody bound to CD34 obtained from the foregoing embodiment can comprise a light chain variable region and a heavy chain variable region. In which, the light chain variable region can comprise an amino acid sequence as set forth in SEQ ID NO: 1 and the heavy chain variable region can comprise an amino acid sequence as set forth in SEQ ID NO: 2.

Further, the amino acid sequences of SEQ ID NO: 1 and SEQ ID NO: 2 can comprise at least one substitute as follows: the amino acid Serine at position 8 of SEQ ID NO: 1 is substituted with Proline (Ser8Pro), the amino acid Leucine at position 41 of SEQ ID NO: 1 is substituted with Glutamic acid (Leu41Glu), the amino acid Threonine at position 58 of SEQ ID NO: 1 is substituted with Lysine (Thr58Lys), the amino acid Asparagine at position 81 of SEQ ID NO: 1 is substituted with Serine (Asn81Ser), the amino acid Glycine at position 108 of SEQ ID NO: 1 is substituted with Threonine (Gly108Thr), the amino acid Glutamic acid at position 5 of SEQ ID NO: 2 is substituted with Valine (Glu5Val), the amino acid Proline at position 9 of SEQ ID NO: 2 is substituted with Alanine (Pro9Ala), the amino acid Lysine at position 74 of SEQ ID NO: 2 is substituted with Threonine (Lys74Thr), and the amino acid Glutamine at position 75 of SEQ ID NO: 2 is substituted with Serine (Gln75Ser).

In still another embodiment, the above-mentioned light chain variable region of the non-human monoclonal antibody bound to CD34 can comprise an amino acid sequence as set forth in SEQ ID NO: 1 and the heavy chain variable region can comprise an amino acid sequence as set forth in SEQ ID NO: 2. In addition, the human sequence with the highest identity to the $V_L$ amino acid sequence of the non-human monoclonal antibody is the light chain variable region sequence (SEQ ID NO: 5), which is composed of human germline V region from IGLV4-69*01 group (SEQ ID NO: 3) and human common sequence J region from IGLJ1*01 (SEQ ID NO: 4). Moreover, the human sequence with the highest identity to the $V_H$ amino acid sequence of the non-human monoclonal antibody is the heavy chain variable region sequence (SEQ ID NO: 8), which is composed of human germline V region from IGHV1-3*01 group (SEQ ID NO: 6) and human common sequence J region from IGHJ4*01 (SEQ ID NO: 7).

After comparison of the foregoing sequences, the provided humanized monoclonal antibody bound to CD34 can comprise a light chain variable region and a heavy chain variable region. In which, the light chain variable region can comprise an amino acid sequence as set forth in SEQ ID NO: 9 and the heavy chain variable region can comprise an amino acid sequence as set forth in SEQ ID NO: 10

Another humanized monoclonal antibody is provided in the disclosure, in which the humanized monoclonal antibody binds to a CD34 antigen and the CD34 antigen can be human CD34 antigen. The foregoing humanized monoclonal antibody can comprise a light chain variable region and a heavy chain variable region. The sequence of the light chain variable region can be any mentioned sequence of light chain variable region of the humanized monoclonal antibody, as well as the sequence of the heavy chain variable region can be any mentioned sequence of heavy chain variable region of the humanized monoclonal antibody. In one embodiment, the above-mentioned humanized monoclonal antibody can be an immunoglobulin G (IgG) antibody, which may include a light chain variable region, a heavy chain variable region, and a human immunoglobulin G conserved region in unilateral.

Further, still another humanized monoclonal antibody is provided in the disclosure. The humanized monoclonal antibody can comprise a light chain variable region and a heavy chain variable region. In which, a nucleotide sequence encoding the amino acid sequence of the light chain variable region can comprise a first nucleotide sequence, and the first nucleotide sequence encodes an amino acid sequence as set forth in SEQ ID NO: 9 or an amino acid sequence with at least 80% sequence identity to the sequence of SEQ ID NO: 9, and a nucleotide sequence encoding the amino acid sequence of the heavy chain variable region can comprise a second nucleotide sequence, and the second nucleotide sequence encodes an amino acid sequence as set forth in SEQ ID NO: 10 or an amino acid sequence with at least 80% sequence identity to the sequence of SEQ ID NO: 10. Moreover, the humanized monoclonal antibody binds to the CD34 antigen. In one embodiment, the foregoing nucleotide sequence encoding the amino acid sequence of the light chain variable region can comprise a nucleotide sequence encoding the amino acid sequence of SEQ ID NO: 9, and the foregoing nucleotide sequence encoding the amino acid sequence of the heavy chain variable region can comprise a nucleotide sequence encoding the amino acid sequence of SEQ ID NO: 10.

The above-mentioned humanized monoclonal antibody can be obtained by the following steps, but it is not limited thereto.

First, the amino acid sequences of non-human monoclonal antibody $V_L$ and $V_H$ are provided. Then, based on the amino acid sequences of the light and heavy chains of the non-humanized monoclonal antibody which binds to the CD34 antigen, the molecular modeling structure of the light and heavy chains of the above-mentioned non-humanized monoclonal antibody was established, as well as the non-conserved surface residues were also determined. In one embodiment, the molecular modeling structure can be performed by the computer-assisted homology simulation.

Thereafter, the human sequence with the highest identity to the variable region amino acid sequence of non-human monoclonal antibody bound to CD34 were searched and the substitutable residues thereof were determined by comparison of the above-mentioned two sequences. Moreover, the nucleotide sequence encoding the variable region amino acid sequence of the non-human monoclonal antibody bound to CD34 can be substituted by site-directed mutagenesis with the nucleotide sequence encoding the amino acid residues corresponding to the position of the aforementioned residues of the human sequence. Then, the nucleotide fragments of the light and heavy chain variable regions of the humanized monoclonal antibody bound to CD34 can be obtained and provided accordingly in the disclosure.

In one embodiment, the non-human monoclonal antibody bound to CD34 can comprise a murine monoclonal antibody. The nucleotide sequence encoding the light chain variable region of the murine monoclonal antibody can comprise the sequence as set forth in SEQ ID NO: 11, and the nucleotide sequence encoding the heavy chain variable region of the murine monoclonal antibody can comprise the sequence as set forth in SEQ ID NO: 12. Further, the nucleotide sequence as set forth in SEQ ID NO: 11 can encode the amino acid sequence as set forth in SEQ ID NO: 1, and the nucleotide sequence as set forth in SEQ ID NO: 12 can encode the amino acid sequence as set forth in SEQ ID NO: 2.

In addition, the nucleotide sequence encoding the light chain variable region of the humanized monoclonal antibody can comprise the sequence as set forth in SEQ ID NO: 13, and the nucleotide sequence encoding the heavy chain variable region of the humanized monoclonal antibody can comprise the sequence as set forth in SEQ ID NO: 14. In which, the nucleotide sequence as set forth in SEQ ID NO: 13 can encode the amino acid sequence as set forth in SEQ ID NO: 9, and the nucleotide sequence as set forth in SEQ ID NO: 14 can encode the amino acid sequence as set forth in SEQ ID NO: 10.

Thereafter, the foregoing nucleotide fragments of the light and heavy chain variable regions of the humanized monoclonal antibody for CD34 of the present disclosure and a known nucleotide fragment of human conserved region were cloned into the suitable expression vectors, respectively.

Then, the expression vectors is subsequently transfected into a suitable host cell, respectively, so that the humanized monoclonal antibody of the disclosure can be expressed by the host cell for binding to CD34.

Moreover, the disclosure still provides a humanized monoclonal antibody, which can comprise a light chain variable region and a heavy chain variable region. In which, a nucleotide sequence encoding the light chain variable region comprises a first nucleotide sequence as set forth in SEQ ID NO: 13 or a first nucleotide sequence with at least 80% sequence identity to the sequence of SEQ ID NO: 13, and a nucleotide sequence encoding the heavy chain variable region comprises a second nucleotide sequence as set forth in SEQ ID NO: 14 or a second nucleotide sequence with at least 80% sequence identity to the sequence of SEQ ID NO: 14. In addition, the humanized monoclonal antibody binds to a CD34 antigen. In one embodiment, the above-mentioned nucleotide sequence encoding the light chain variable region comprises the sequence of SEQ ID NO: 13, and the nucleotide sequence encoding the heavy chain variable region comprises the sequence of SEQ ID NO: 14.

Otherwise, the binding affinity to CD34 of any the foregoing humanized monoclonal antibody in the disclosure may be about 10-20 nM, preferably about 5-10 nM.

In one embodiment, the above-mentioned humanized monoclonal antibody can bind to a solid support, a functional group or a biomolecule to facilitate the possible subsequent process, such as the separation step. In which, the solid support can be a bead, a chip or a plate, but it is not limited thereto. The functional group can be an amino group (—NH$_2$), a mercapto group (—SH), a carboxyl group (—COOH) or a hydroxyl group (—OH), but it is not limited thereto. The biomolecule can be a biotin, an avidin or a streptavidin, but it is not limited thereto. The bead can be commercially available iron oxide particles (TOP), superparamagnetic iron oxide particles (SPIO) or other magnetic micro- or nano-beads. In one example, as the biomolecule for binding of the above-mentioned humanized monoclonal antibody is biotin, a bead with anti-biotin molecules on the surface will be the better choice.

In one embodiment of the disclosure, the humanized monoclonal antibody can further comprise a color material. The color material can be fluorochromes, such as fluorescein isothiocyanate (FITC), Alexa Fluor dye, cyanine dye (cyanine dye, C2, Cy3 and Cy5) or the like, fluorescent protein, such as phytochrome-based near-infrared fluorescent protein (iRFP), bioluminescence, such as firefly luciferase (Fluc) or Gaussia luciferase (Gluc), nanoparticles, such as quantum dots, iron oxide magnetic beads (TOP), superparamagnetic iron oxide beads (SPIO) or the like, but it is not limited thereto.

In addition, the above-mentioned humanized monoclonal antibody has the effect on inhibition of angiogenesis. In one embodiment of the disclosure, the aim of inhibiting angiogenesis can be achieved by performing the humanized monoclonal antibody binding to the CD34 protein expressed on cells.

Hence, in another embodiment of the disclosure, a method for treating angiogenesis and/or angiogenesis-related diseases is provided. The method for treating angiogenesis and/or angiogenesis-related diseases may include administering an effective amount of any above-mentioned humanized monoclonal antibody to a subject in need thereof to treat angiogenesis and/or angiogenesis-related diseases.

Moreover, the above-mentioned angiogenesis-related diseases can be cancer, neovascular glaucoma, age-related macular degeneration (AMD or ARMD) or the like, but it is not limited thereto.

In the above-mentioned method for treating to treat angiogenesis and/or angiogenesis-related diseases of the present disclosure, the subject may include a mammal, but it is not limited thereto. Examples of the mammal may include, but are not limited to, a human, an orangutan, a monkey, a horse, a donkey, a dog, a cat, a rabbit, a guinea pig, a rat, and a mouse. In one embodiment, in above-mentioned method for treating to treat angiogenesis and/or angiogenesis-related diseases of the present disclosure, the subject is a human.

Furthermore, the humanized monoclonal antibody of the disclosure may depend on the need to optionally bind to a solid support, a functional group or a biomolecule. Also, the description of the solid support, functional group and biomolecule are as described above and no need to repeat them herein.

Examples

A. Materials and Methods

1. Materials

Mouse QBEND/10 was purchased from AbD Serotec. Ammonium bicarbonate, Dithiolthreitol (DTT), Iodoacetamide (IAM), Formic Acid (FA), Thermolysin and Subtilisin were purchased from Sigma-Aldrich. Urea and Acetonitrile (ACN) were purchased from J. T Baker. Trypsin and Chymotrypsin were purchased from Promega. Endoproteinase Glu-C (Glu-C) and Peptide N-glycosidase F (PNGase F) were purchased from New England BioLabs and Roche, respectively. Moreover, 4-12% and 4-20% NuPAGE Bis-Tris polyacrylamide gel was purchased from Invitrogen. Amicon Ultra Centrifugal Filters, 100 kDa cut-off, were purchased from Millipore.

2. Methods (1) Enzymatic Digestion and Deglycosylation of QBEND/10

Mouse QBEND/10 was first processed for detergent removal and buffer exchange into 50 mM ammonium bicarbonate buffer solution by 100 kDa cut-off Amicon Ultra Centrifugal Filters. Next, QBEND/10 was denatured with 6 M urea, reduced with 10 mM DTT at 37° C. for 1 hour and alkylated with 50 mM Iodoacetamide (IAM) for 30 mins in dark at room temperature. Afterwards, the resulting protein was individually digested with trypsin, endoproteinase Glu-C, thermolysin, chymotrypsin and subtilisin at 37° C. for 18 hours (protein:enzyme=20:1). One aliquot of trypsin digest was added with Glu-C for 20-hour digestion at 37° C. Thereafter, PNGase F was added for deglycosylation reaction overnight. The samples were subsequently diluted and acidified to 0.1% FA for liquid chromatography mass spectrometry (LC-MS) analysis.

(2) In-Gel Tryptic Digestion

In a parallel experiment, a mini gel (8 cm×8 cm and 4-20% NuPAGE Bis-Tris polyacrylamide gel) was used for separation through sodium dodecyl sulfate polyacrylamide gel electrophoresis (SDS-PAGE), followed by Coomassie Brilliant Blue R-250 staining. After that, two bands containing proteins with apparent molecular masses of approximately 25 kDa and 50 kDa were excised from the gel. Further, the steps of wash, in-gel reduction, alkylation, and digestion with trypsin overnight were performed sequentially.

(3) Liquid Chromatography-Tandem Mass Spectrometry (LC-MS/MS) Analysis

The samples were analyzed with a Q Exactive mass spectrometer (Thermo Scientific) coupled with an Ultimate 3000 RSLC system (Dionex). The LC separation was performed using the C18 column (Acclaim PepMap RSLC, 75 μm×150 mm, 2 μm, 100 Å) with the linear gradient from 1% to 25% of mobile phase B for 40 min, 25% to 60% of mobile phase B for 3 min, and 60% to 80% of mobile B for 2 min in a total of 70 min separation time (Mobile phase A: 5% ACN/0.1% FA; Mobile phase B: 95% ACN/0.1% FA). Next, full MS scan was performed with the range of m/z 350-2000, and the 10 most intense ions from the MS scan were subjected to fragmentation for obtaining the MS/MS spectra. Moreover, the raw data were processed into peak lists by Proteome Discoverer 1.3 for performing the following Mascot database search.

(4) Database Search and De Novo Sequencing

A customized database is made and established by collecting the sequences of immunoglobulins originated from the database of National Center for Biotechnology Information (NCBI). The database was searched by Mascot version 2.4.0. Next, Carbamidomethyl (C) was selected as fixed modification and Deamidated (NQ), Oxidation (M), Pyroglutamate (N-term Q) were included as variable modifications. In which, up to five missed cleavages were allowed for each enzyme digestion, and ±5 ppm and ±0.02 Da were used as the mass tolerance window for parent ion and fragment ion, respectively. Then, error tolerant search was performed, in which all modifications and sequence variations were considered. The MS/MS spectra with high intensities were manually sequenced if they had not been identified by Mascot. Thereafter, a customized computational algorithm was constructed to group the observed peptides into heavy chain or light chain and then align the peptides into a complete sequence. The results were sent back to Mascot as a new database for protein identification and error tolerant search. Otherwise, the process was repeated iteratively until the protein sequence with the highest score was obtained. All MS/MS spectra in this study were further manually validated to assure its quality.

(5) Molecular Modeling

Molecular modeling of variable fragment (Fv) of murine QBEND/10 was performed using PIGS (Prediction of ImmunoGlobulin Structure) (http://www.biocomputing.it/pigs) (Marcatili P, Rosi A, Tramontano A. PIGS: automatic prediction of antibody structures. Bioinformatics. 2008; 24(17):1953-4; Marcatili P, Olimpieri P P, Chailyan A, Tramontano A. Antibody structural modeling with prediction of immunoglobulin structure (PIGS). Nature protocols. 2014; 9(12):2771-83.) web server via single sequence submission. The structure model of mouse QBEND/10 Fv region was generated from the corresponding amino acid sequence using PIGS with default settings. Best heavy and light chain templates were chosen from 20 templates displayed. The Protein Data Bank (PDB) codes of 2GKI H (Kim Y R, Kim J S, Lee S H, Lee W R, Sohn J N, Chung Y C, et al. Heavy and light chain variable single domains of an anti-DNA binding antibody hydrolyze both double- and single-stranded DNAs without sequence specificity. The Journal of biological chemistry. 2006; 281(22):15287-95) and 2QHR L (Lee J E, Kuehne A, Abelson D M, Fusco M L, Hart M K, Saphire E O. Complex of a protective antibody with its Ebola virus GP peptide epitope: unusual features of a V lambda x light chain. Journal of molecular biology. 2008; 375(1):202-16), respectively, of 86.67% and 94.92% sequence identity with mouse QBEND/10 $V_H$ and $V_L$, were used to model the three-dimensional (3D) structure of mouse QBEND/10. For automated construction of the 3D structure of Fv region of mouse QBEND/10, a canonical loop grafting approach was used for all complementarity-determining regions (CDRs) L1 to L3 and H1 to H3. Further, the position of conserved amino acid side chains was maintained, while the non-conserved amino acid side chains were modeled with SCWRL 4.0 (Krivov G G, Shapovalov M V, Dunbrack R L, Jr. Improved prediction of protein side-chain conformations with SCWRL4. Proteins. 2009; 77(4):778-95). Moreover, energy minimization was performed by using Swiss-PdbViewer application (Guex N, Peitsch M C. SWISS-MODEL and the Swiss-PdbViewer: an environment for comparative protein modeling. Electrophoresis. 1997; 18(15):2714-23).

(6) Humanization of QBEND/10

Humanization of mouse QBEND/10 was performed by using resurfacing approach (Padlan E A. A possible procedure for reducing the immunogenicity of antibody variable domains while preserving their ligand-binding properties. Molecular immunology. 1991; 28(4-5):489-98). The $V_H$, $V_L$ and CDRs were numbered and identified as per Kabat definitions (Kabat E A, National Institutes of H, Columbia U. Sequences of proteins of immunological interest. Bethesda, Md.: U.S. Dept. of Health and Human Services, Public Health Service, National Institutes of Health; 1991). First, the generated Fv model of mouse QBEND/10 was used to identify the surface accessible residues by performing the Swiss-PdbViewer (Guex N, Peitsch M C. SWISS-MODEL and the Swiss-PdbViewer: an environment for comparative protein modeling. Electrophoresis. 1997; 18(15):2714-23) with a threshold that was set to 30% (Pedersen J T, Henry A H, Searle S J, Guild B C, Roguska M, Rees A R. Comparison of surface accessible residues in human and murine immunoglobulin Fv domains. Implication for humanization of murine antibodies. Journal of molecular biology. 1994; 235(3):959-73). Second, the sequence of mouse QBEND/10 variable heavy and light chain was searched by NCBI IgBLAST against the human IgG germline database (http://www.ncbi.nlm.nih.gov/igblast/). Human germline V sequences with highest identity to mouse $V_H$ and $V_L$ regions were used. The J region of the heavy and light chains was selected from the most identical human consensus sequence. Then, these important surface residues of framework regions were exchanged manually to those found on the selected human IgG germline sequence. These side chains were rotated manually to evaluate the stable side chain conformation and then subjected to energy minimization by performing Swiss-PdbViewer. Finally, the sequence composition for Fv region of resurfaced QBEND/10 was assembled. Two resulting models, murine and humanized QBEND/10, were analyzed, visualized and superimposed with Swiss-PdbViewer (Guex N, Peitsch M C. SWISS-MODEL and the Swiss-PdbViewer: an environment for comparative protein modeling. Electrophoresis. 1997; 18(15):2714-23). Moreover, the structure changes in the CDRs were determined by the superimposed result.

(7) Construction of Recombinant Plasmid

The DNA sequences of QBEND/10 $V_H$ and $V_L$ were synthesized separately by GenScript (GenScript USA Inc., Piscataway, N.J., USA). In which, the coding region of heavy chain is composed of an N-terminal QBEND/10 $V_H$ and a C-terminal human IgG1 constant region (CHL hinge, CH2 and CH3) nucleotide sequence. The synthetic gene was prepared by overlapping polymerase chain reaction (PCR). Then, the PCR product flanked with EcoRV and BamHI sites was cloned into the expression vector pSecTag2/Hygro (Thermo Fisher Scientific, Waltham, Mass., USA) at the same sites. Thereafter, the entire heavy chain DNA for QBEND/10 was cloned in-frame with the N-terminal mouse Ig kappa-chain V-J2-C signal peptide of the pSecTag2/Hygro expression vector for secretion. On the other hand, the coding region of light chain is composed of an N-terminal QBEND/10 $V_L$ and a C-terminal lambda light chain constant region nucleotide sequence. The synthetic gene was prepared by overlapping PCR. Further, the PCR product was cloned into the expression vector pcDNA3.3-TOPO TA (Thermo Fisher Scientific, Waltham, Mass., USA). Next, the entire light chain DNA for QBEND/10 was also cloned in-frame with the N-terminal murine Ig kappa-chain V-J2-C signal peptide for secretion.

(8) Expression and Purification of Antibodies

The recombinant QBEND/10 antibodies were obtained by stable co-transfection of expression constructs in mouse myeloma NSO cells (European Collection of Animal Cell Cultures, Wiltshire, UK) by using the reagent Effectene (QIAGEN Inc., Valencia, Calif., USA) according to the manufacturer's instructions. After selection with 400 µg/ml Hygromycin B (Thermo Fisher Scientific, Waltham, Mass., USA) and 800 µg/ml G418 (Thermo Fisher Scientific, Waltham, Mass., USA) for 4 weeks, a stable clone was cultured in a shaker flask at an initial seeding density of $5 \times 10^5$ cells/ml in a chemically defined medium HyClone CDM4NSO (Hyclone, GE Healthcare, South Logan, Utah, USA) containing 2% fetal bovine serum. The above-mentioned culture was maintained at 130 rpm for 5 days at 37° C. Then, the recombinant antibodies were purified from the supernatant by human-IgG affinity column (IgSelect; GE Healthcare, South Logan, Utah, USA).

(9) SDS-PAGE

SDS-PAGE was performed by a 4-12% NuPAGE Bis-Tris polyacrylamide gel with 3-morpholinopropanesulfonic acid (MOPS) as the running buffer (Thermo Fisher Scientific, Waltham, Mass., USA). In addition, proteins were stained with Coomassie Brilliant Blue R-250.

(10) ELISA

The protein concentrations were estimated by performing the procedure of Bradford (Bradford M M. A rapid and sensitive method for the quantitation of microgram quantities of protein utilizing the principle of protein-dye binding. Analytical biochemistry. 1976; 72:248-54). In Brief, a Nunc™ MaxiSorp 96-well plate (Thermo Fisher Scientific, Waltham, Mass., USA) was coated with human CD34 protein (Fc tag) (Sino Biological Incorporation, Beijing, China) in a volume of 50 µl at a concentration of 5 µg/ml and incubated at 4° C. for 18 hours. After blocking with StartingBlock™ blocking buffer (Thermo Fisher Scientific, Waltham, Mass., USA) and washing with PBS containing 0.01% Tween-20 (PBST) three times, the samples were added to the plates and incubated for 1 hour at 37° C. After washing, the plates were incubated with horseradish peroxidase (HRP)-conjugated anti-human lambda light chain antibody (Bethyl Laboratories, Inc., Montgomery, Tex.) for 1 hour at room temperature (RT), followed by washing with PBST. Subsequently, 3,3',5,5'-Tetramethylbenzidine (TMB) was added to induce the color reaction. After stopping the reaction with 1 N HCl, the absorbance was read at 450 nm on a microplate reader. All measurements were performed in duplicate.

(11) Surface Plasmon Resonance (SPR)

The binding kinetics of QBEND/10 antibodies to the human CD34 protein (Fc tag) (Sino Biological Incorporation, Beijing, China) were measured by performing the Biacore system (Biacore X, GE Healthcare, South Logan, Utah, USA) in the electrophoresis running buffer HBS-EP (10 mM HEPES, pH 7.4; 150 mM NaCl; 3 mM EDTA; 0.005% surfactant P20). In Brief, human CD34 protein was immobilized onto a CMS sensor chip via amine coupling to a level of 1200 response units (RU), and purified antibodies with different concentrations were injected at a flow rate of 30 µl/min. The surface was regenerated by injection of 15 µl of 10 mM glycine-HCl, pH 2.5. Then, the sensorgrams obtained at each concentration were evaluated by the program BIA Evaluation 3.2 (GE Healthcare, South Logan, Utah, USA). The binding data were fitted with a 2:1 (bivalent) binding model to calculate the affinity constant $K_D$, which was defined as the ratio of dissociation rate $(k_{off})$/association rate $(k_{on})$.

(12) Cell Culture

Human umbilical vein endothelial cells (HUVECs) were obtained from the American Type Cell Culture (ATCC, Manassas, Va.). For expansion, cells were grown in endothelial cell medium (ECM) supplemented with 5% fetal bovine serum (FBS), 1% endothelial cell growth supplement (ECGS) and 1% penicillin/streptomycin (P/S) at 37° C., 5% $CO_2$, in which ECM, ECGS and antibiotics were obtained from ScienCell Research Laboratory.

(13) Tube Formation Assay

The assay was performed by utilizing growth factor-reduced Matrigel (, BD Biosciences), in which Matrigel was added to 15-well microslides (ibidi, Germany) and stood at 37° C. for 1 hour for solidification. Subsequently, sub-confluent HUVECs were pre-stained with 10 µg/ml $DiIC_{12}$ (3) fluorescent dye (BD Biosciences) at 37° C. for 1 hour and then harvested with trypsin/EDTA. To evaluate the effect of mouse or humanized QBEND/10, HUVECs were re-suspended in ECM-basal medium in the presence or absence of QBEND/10 antibody with various concentrations, and then seeded onto the layer of Matrigel at a cell number of $8 \times 10^3$ cells per well. After 18 hours of incubation, tubular network structures were visualized and photographed by the inverted fluorescence microscope. The cell-covered area or tube length were quantified by performing the ImageJ software.

B. Results

1. Treatment of Endothelial Cells with Mouse QBEND/10 Impairs Tube Formation

Since $CD34^{-/-}$ mice exhibit abnormal vessel morphology (Maltby S, Freeman S, Gold M J, Baker J H, Minchinton A I, Gold M R, et al. Opposing roles for CD34 in B16 melanoma tumor growth alter early stage vasculature and late stage immune cell infiltration. PloS one. 2011; 6(4): e18160), the effect of mouse QBEND/10 on tube formation in HUVECs was analyzed. HUVECs tube formation assay is an in vitro analysis for angiogenesis, which recapitulates some angiogenesis steps and has been used for many years (Kubota Y, Kleinman H K, Martin G R, Lawley T J. Role of laminin and basement membrane in the morphological differentiation of human endothelial cells into capillary-like structures. The Journal of cell biology. 1988; 107(4):1589-98; Arnaoutova I, George J, Kleinman H K, Benton G. The endothelial cell tube formation assay on basement membrane turns 20: state of the science and the art. Angiogenesis. 2009; 12(3):267-74). As shown in FIG. 1, treatment of HUVECs with 40 µg/ml mouse QBEND/10 showed a significant reduction in the number of cell-covered area as compared to PBS control group (* represents p<0.05).

2. De Novo Protein Sequencing of Variable Fragments of Mouse QBEND/10

LC-MS/MS based techniques have emerged as an important tool for protein identification (Olsen J V, Macek B, Lange O, Makarov A, Horning S, Mann M. Higher-energy C-trap dissociation for peptide modification analysis. Nature methods. 2007; 4(9):709-12; Syka J E, Coon J J, Schroeder M J, Shabanowitz J, Hunt D F. Peptide and protein sequence analysis by electron transfer dissociation mass spectrometry. Proceedings of the National Academy of Sciences of the United States of America. 2004; 101(26):9528-33; Guthals A, Bandeira N. Peptide identification by tandem mass spectrometry with alternate fragmentation modes. Molecular & cellular proteomics: MCP. 2012; 11(9):550-7). Detail information regarding the peptide sequences can be obtained by the assignment of fragment ions provided by MS/MS spectra. Mascot is so far the most popular search engine and its probability based scoring algorithm has been well accepted. Hence, Mascot score was adopted in this disclosure as a reference of confidence for protein identification and de novo sequencing.

Moreover, to achieve greater sequence coverage, in-solution digestion by using several enzymes and in-gel digestion with trypsin for the separated heavy and light chains were performed. LC-MS/MS was used to analyze all the resulting peptides and peak lists generated for iterative database search and error-tolerant search against customized databases. Only those peptides with high quality MS/MS spectra (ion score ≥30) were listed. The theoretical tryptic peptides and sequences for QBEND/10 $V_L$ and $V_H$ segments are listed in Table 1 and Table 2.

TABLE 1

Theoretical peptides and sequences of QBEND/10 light chains obtained by trypsin digestion

| Theoretical M.W. | Peptide No. | Amino acid No. | Sequence |
|---|---|---|---|
| 1880.9843 | L1 | 1-19 | QLVLTQSSSASFSLGASAK (SEQ ID NO: 15) |
| 1144.5659 | L2 | 20-29 | LTCTLSSQHR (SEQ ID NO: 16) |
| 2003.0516 | L3 | 30-45 | TFTIEWYQQQPLKPPK (SEQ ID NO: 17) |
| 809.4105 | L4 | 46-51 | YVMELR (SEQ ID NO: 18) |
| 146.1055 | L5 | 52-52 | K |
| 1312.5643 | L6 | 53-65 | DGSHSTGDGIPDR (SEQ ID NO: 19) |
| 969.4152 | L7 | 66-75 | FSGSSSGADR (SEQ ID NO: 20) |
| 2639.3152 | L8 | 76-99 | YLSISNIQPEDEAIYICGVGNTIK (SEQ ID NO: 21) |
| 1330.6557 | L9 | 100-111 | EQFVYVFGGGTK (SEQ ID NO: 22) |
| 840.5069 | L10 | 112-119 | VTVLGQPK (SEQ ID NO: 23) |
| 1731.8930 | L11 | 120-135 | STPTLTVFPPSSEELK (SEQ ID NO: 24) |
| 389.1910 | L12 | 136-138 | ENK |
| 2092.1027 | L13 | 139-158 | ATLVCLISNFSPSGVTVAWK (SEQ ID NO: 25) |
| 1699.8377 | L14 | 159-175 | ANGTPITQGVDTSNPTK (SEQ ID NO: 26) |
| 446.2125 | L15 | 176-179 | EGNK (SEQ ID NO: 27) |
| 1824.8617 | L16 | 180-194 | FMASSFLHLTSDQWR (SEQ ID NO: 28) |
| 2017.8799 | L17 | 195-212 | SHNSFTCQVTHEGDTVEK (SEQ ID NO: 29) |
| 818.3844 | L18 | 213-220 | SLSPAECL (SEQ ID NO: 30) |

TABLE 2

Theoretical peptides and sequences of QBEND/10 heavy chains

| Theoretical M.W. | Peptide No. | Amino acid No. | Sequence |
|---|---|---|---|
| 1993.0844 | H1 | 1-19 | QVQLEQSGPELVKPGASVK (SEQ ID NO: 31) |
| 467.1872 | H2 | 20-23 | MSCK (SEQ ID NO: 32) |
| 1757.8777 | H3 | 24-38 | ASGYTFTSYVIHWVK (SEQ ID NO: 33) |
| 2407.1808 | H4 | 39-59 | QKPGQGLEWLGYTNPYNDVTK (SEQ ID NO: 34) |
| 552.2544 | H5 | 60-63 | YNEK (SEQ ID NO: 35) |
| 293.1739 | H6 | 64-65 | FK |
| 293.1739 | H7 | 66-67 | FK |
| 734.3810 | H8 | 68-74 | ATLTSDK (SEQ ID NO: 36) |
| 2709.1574 | H9 | 75-98 | QSTTAYMEFSSLTSEDSAVYYCAR (SEQ ID NO: 37) |
| 2639.2366 | H10 | 99-122 | YGGLWLYAMDYWGQGTSVTVSSAK (SEQ ID NO: 38) |
| 2802.4295 | H11 | 123-150 | TTPPSVYPLAPGSAAQTNSMVTLGCLVK (SEQ ID NO: 39) |
| 6497.1325 | H12 | 151-212 | GYFPEPVTVTWNSGSLSSGVHTFPAVLQSDLYTLSSSVTVPSSTWPSETVTCNVAHPASSTK (SEQ ID NO: 40) |
| 360.2009 | H13 | 213-215 | VDK |
| 146.1055 | H14 | 216-216 | K |
| 483.3169 | H15 | 217-220 | IVPR (SEQ ID NO: 41) |
| 2693.3089 | H16 | 221-245 | DCGCKPCICTVPEVSSVFIFPPKPK (SEQ ID NO: 42) |
| 1099.6488 | H17 | 246-255 | DVLTITLTPK (SEQ ID NO: 43) |
| 1061.5791 | H18 | 256-265 | VTCVVVDISK (SEQ ID NO: 44) |
| 2844.2990 | H19 | 266-289 | DDPEVQFSWFVDDVEVHTAQTQPR (SEQ ID NO: 45) |
| 1156.5149 | H20 | 290-298 | EEQFNSTFR (SEQ ID NO: 46) |
| 1852.9141 | H21 | 299-314 | SVSELPIMHQDWLNGK (SEQ ID NO: 47) |
| 422.2165 | H22 | 315-317 | EFK |
| 277.1209 | H23 | 318-319 | CR |
| 1242.6608 | H24 | 320-331 | VNSAAFPAPIEK (SEQ ID NO: 48) |
| 447.2693 | H25 | 332-335 | TISK (SEQ ID NO: 49) |
| 247.1532 | H26 | 336-337 | TK |

TABLE 2-continued

Theoretical peptides and sequences of QBEND/10 heavy chains

| Theoretical M.W. | Peptide No. | Amino acid No. | Sequence |
|---|---|---|---|
| 456.2808 | H27 | 338-341 | GRPK (SEQ ID NO: 50) |
| 1209.6757 | H28 | 342-352 | APQVYTIPPPK (SEQ ID NO: 51) |
| 605.2843 | H29 | 353-357 | EQMAK (SEQ ID NO: 52) |
| 261.1325 | H30 | 358-359 | DK |
| 3574.6424 | H31 | 360-389 | VSLTCMITDFFPEDITVEWQWNAQPAENYK (SEQ ID NO: 53) |
| 1964.8826 | H32 | 390-406 | NTQPIMDTDGSYFVYSK (SEQ ID NO: 54) |
| 600.3595 | H33 | 407-411 | LNVQK (SEQ ID NO: 55) |
| 2847.2783 | H34 | 412-436 | SNWEAGNTFTCSVLHEGLHNHHTEK (SEQ ID NO: 56) |
| 811.4188 | H35 | 437-444 | SLSHSPGK (SEQ ID NO: 57) |

Figure 2A:
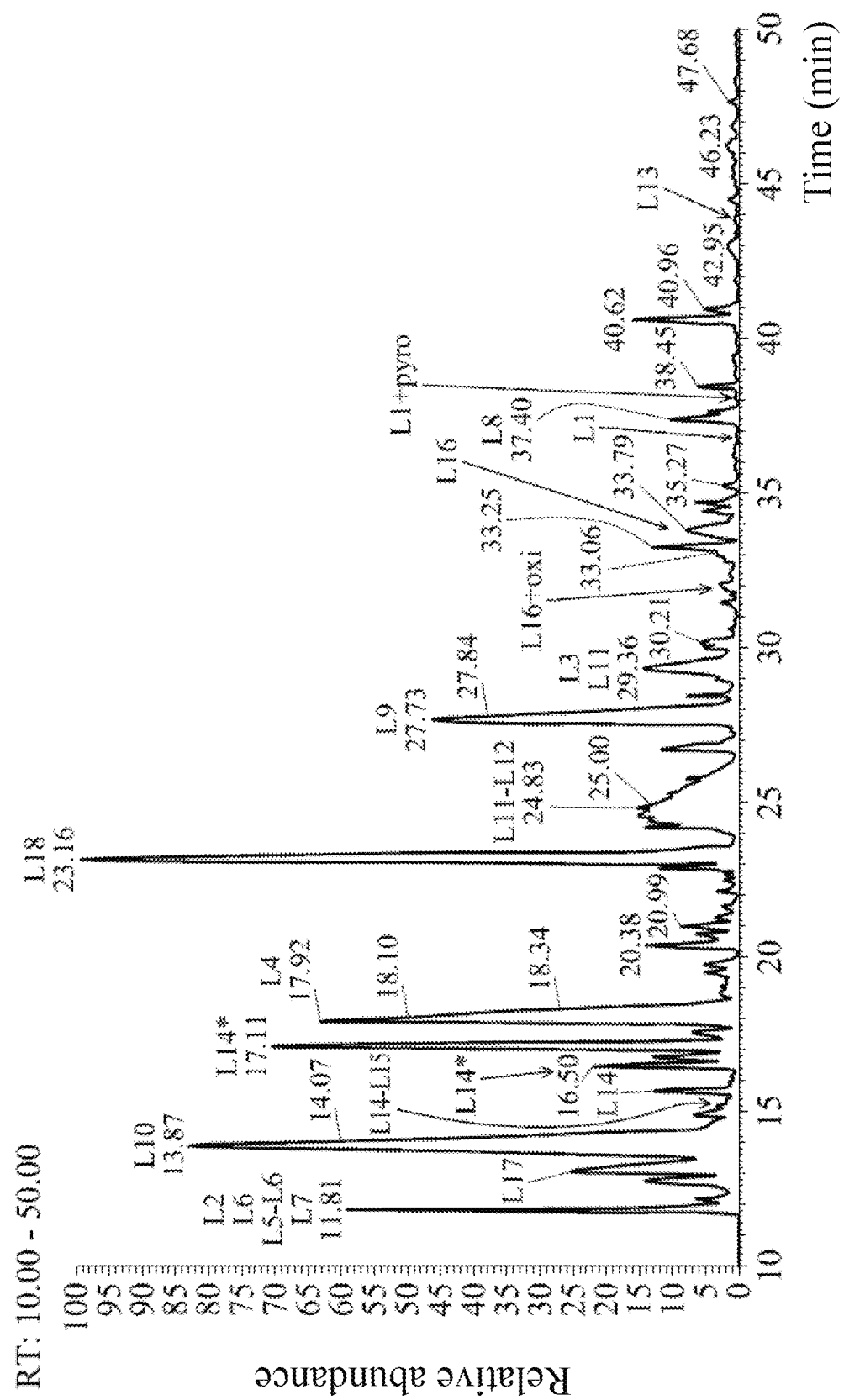
FIGS. 2A and 2B show the base peak intensity (BPI) chromatogram of QBEND/10 light chain (A) and heavy chain (B), respectively, from trypsin digestion. In which, "Ln" and "Hn" denote the nth peptide counted from the N-terminal of QBEND/10 light chain and heavy chain, respectively, stars annotate deamidated peptides, "pyro" indicates Pyro-glutamate at Glutamine (Q), and "oxi" denotes oxidation at Methionine (M).
Figure 2B:
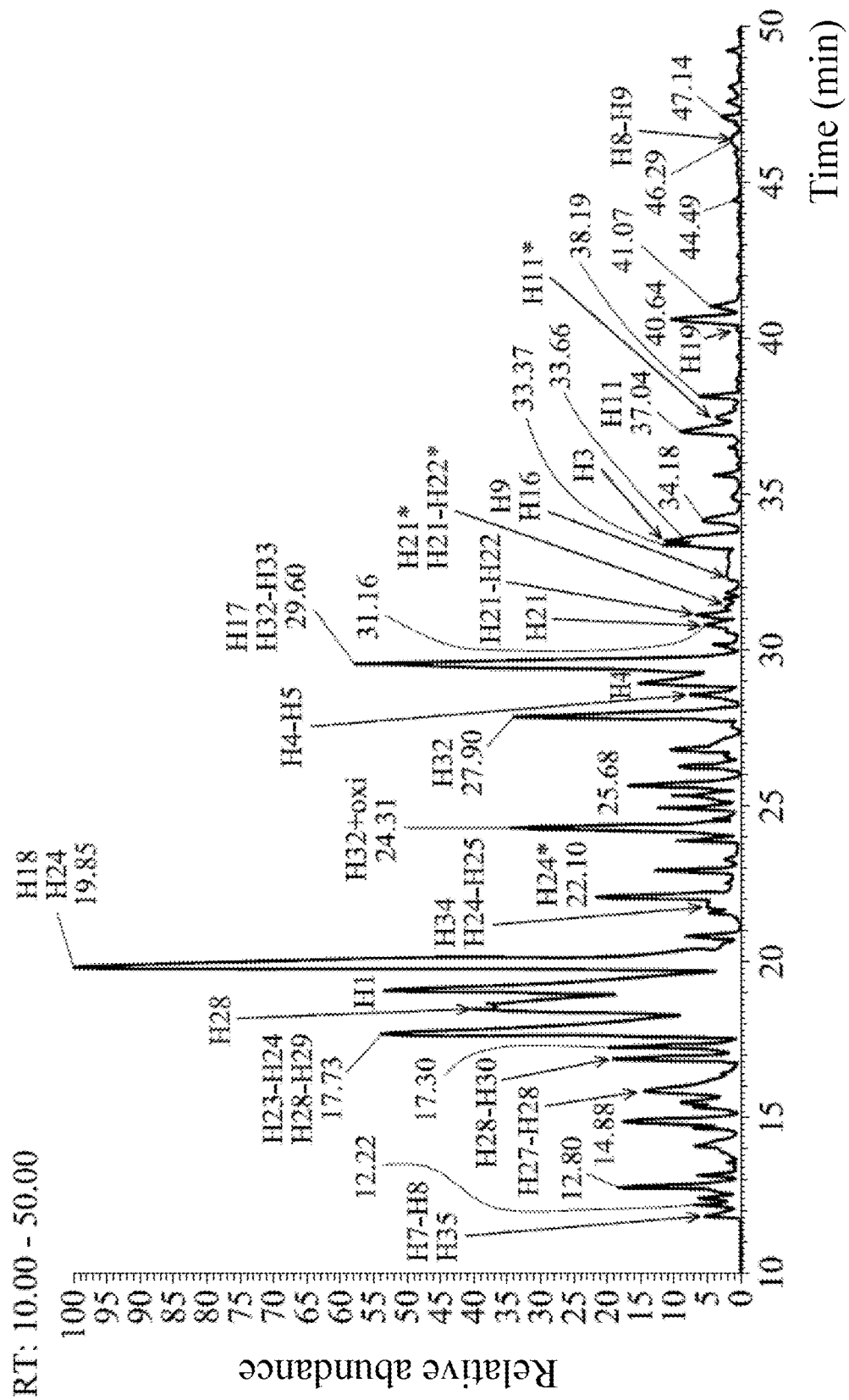

The base peak intensity (BPI) chromatograms of QBEND/10 light chain heavy chains digested by trypsin are shown in FIGS. 2A and 2B. Ln and Hn indicate the nth tryptic peptide assigned from the N-terminal of light chain and heavy chain, respectively. Each peak was identified and assigned according to FIGS. 2A and 2B.

Furthermore, identification results of the variable region of light chain and heavy chain from multiple enzyme digestion are aligned and illustrated in FIGS. 3A and 3B.

3. Molecular Modeling of QBEND/10

Figure 4:
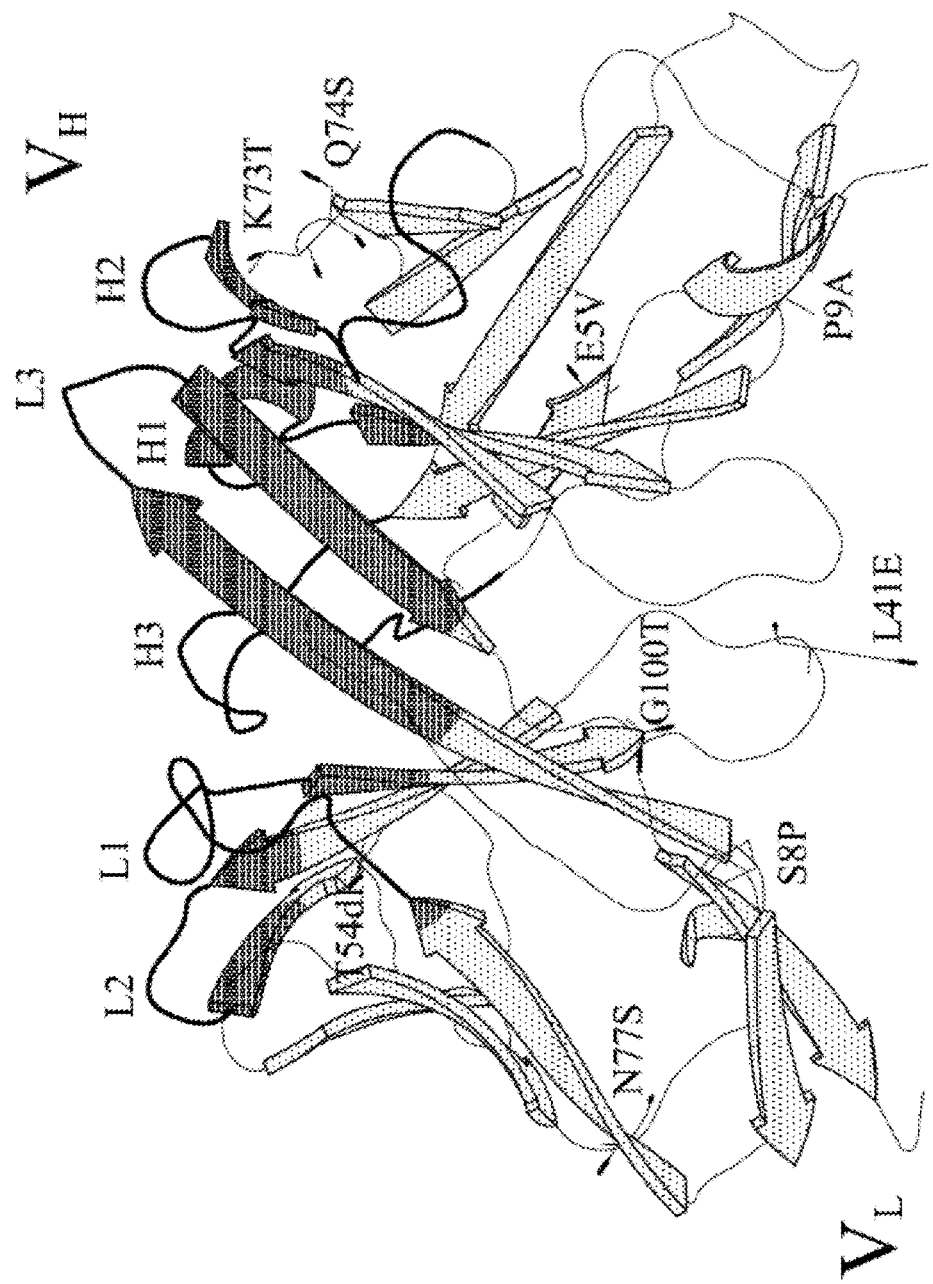
FIG. 4 shows the molecular model of the QBEND/10 variable regions. The 3D structure of murine QBEND/10 FAT region is generated by web-based antibody structure prediction program PIGS (Prediction of Immunoglobulin Structure: http://www.biocomputing.it/pigs). Nine amino acids (in boldface), including four residues in the $V_H$ framework and five residues in the $V_L$ framework, are substituted with human germline residues. CDR loops are shown in thick line.

Molecular modeling of murine QBEND/10 was performed by PIGS (Prediction of ImmunoGlobulin Structure) (http://www.biocomputing.it/pigs) (Marcatili P, Rosi A, Tramontano A. PIGS: automatic prediction of antibody structures. Bioinformatics. 2008; 24(17):1953-4; Marcatili P, Olimpieri P P, Chailyan A, Tramontano A. Antibody structural modeling with prediction of immunoglobulin structure (PIGS). Nature protocols. 2014; 9(12):2771-83) as described in Materials and Methods. The final refined 3D structure of the Fv region as demonstrated in FIG. 4 was viewed by the Swiss-PdbViewer (aka DeepView) application (Guex N, Peitsch M C. SWISS-MODEL and the Swiss-PdbViewer: an environment for comparative protein modeling. Electrophoresis. 1997; 18(15):2714-23). Both the Fv regions of the light and heavy chains of murine QBEND/10 were modeled using the best matches with the highest sequence identities of known templates from different structures.

In addition, the Protein Data Bank (PDB) codes of the templates for murine QBEND/10 Fv regions are as follows (the sequence identity is indicated in parentheses): 2GKI (Kim Y R, Kim J S, Lee S H, Lee W R, Sohn J N, Chung Y C, et al. Heavy and light chain variable single domains of an anti-DNA binding antibody hydrolyze both double- and single-stranded DNAs without sequence specificity. The Journal of biological chemistry. 2006; 281(22):15287-95) for the heavy-chain (86.67%), 2QHR (Lee J E, Kuehne A, Abelson D M, Fusco M L, Hart M K, Saphire E O. Complex of a protective antibody with its Ebola virus GP peptide epitope: unusual features of a V lambda x light chain. Journal of molecular biology. 2008; 375(1):202-16) for the light chain (94.92%), 2QHR for CDR-L1 (SEQ ID NO: 72) (75%), 2QHR for CDR-L2 (SEQ ID NO: 73) (85.71%), 2QHR for CDR-L3 (SEQ ID NO: 74) (92.31%), 2GKI for CDR-H1 (SEQ ID NO: 75) (90%), 2GKI for CDR-H2 (SEQ ID NO: 76) (82.35%), and 2GKI for CDR-H3 (SEQ ID NO: 77) (45.45%). All CDRs were modeled on the basis of canonical conformations defined for those particular canonical structure classes.

4. Humanization of QBEND/10

Through NCBI IgBLAST, the human germline V region from the IGLV4-69*01 (SEQ ID NO: 4) and IGHV1-3*01 (SEQ ID NO: 7) groups showed the highest identity to mouse QBEND/10 $V_L$ (70.1%) and $V_H$ (67.3%), respectively. The sequence alignment of the mouse and human templates was illustrated in FIGS. 5A and 5B. The J regions for the heavy chain (IGHJ4*01; Sequence: WGQGTLVTVSS (SEQ ID NO: 7)) and the light chain (IGLJ1*01; Sequence: FGTGTKVTVL (SEQ ID NO: 4)) were selected from the most identical human consensus sequences, which showed one mismatched residue each for $V_H$ and $V_L$. Furthermore, the model of QBEND/10 as shown in FIG. 6 was used to identify the surface accessible residues.

In the case of QBEND/10 $V_L$, 35 amino acids were identified as the surface accessible amino acids (as shown in FIG. 5A). Excluding CDRs, only 5 of the 35 amino acids differed from the human germline sequence and were adapted to the human version. That is, the 5 accessible amino acids differed from the human germline were substituted with their corresponding amino acids.

According to the coding method of residue numbers defined by Kabat et al., the QBEND/10 $V_L$ (SEQ ID NO: 1) was coded and the above-mentioned 5 amino acids were substituted as follows: the amino acid Serine at position 8 of Kabat's coded QBEND/10 $V_L$ was substituted with Proline (Ser8Pro), the amino acid Leucine at position 41 of Kabat's coded QBEND/10 $V_L$ was substituted with Glutamic acid (Leu41Glu), the amino acid Threonine at position 54d of Kabat's coded QBEND/10 $V_L$ was substituted with Lysine (Thr54dLys), the amino acid Asparagine at position 77 of Kabat's coded QBEND/10 $V_L$ was substituted with Serine (Asn77Ser), and the amino acid Glycine at position 100 of Kabat's coded QBEND/10 $V_L$ was substituted with Threonine (Gly100Thr).

Nevertheless, when according to the position of each amino acid of the $V_L$ sequence (SEQ ID NO: 1) as shown in sequence listing, the above-mentioned 5 amino acids were substituted as follows: the amino acid Serine at position 8 of SEQ ID NO: 1 was substituted with Proline (Ser8Pro), the amino acid Leucine at position 41 of SEQ ID NO: 1 was substituted with Glutamic acid (Leu41Glu), the amino acid Threonine at position 58 of SEQ ID NO: 1 was substituted with Lysine (Thr58Lys), the amino acid Asparagine at position 81 of SEQ ID NO: 1 was substituted with Serine (Asn81Ser), and the amino acid Glycine at position 108 of SEQ ID NO: 1 was substituted with Threonine (Gly108Thr). In addition, the sequence obtained by performing the above-mentioned substitutions is defined as SEQ ID NO: 9.

As for the QBEND/10 $V_H$, as shown in FIG. 5B, 28 amino acids in the $V_H$ of QBEND/10 were identified as the surface accessible residues. Excluding CDR regions, only 4 of 28 surface accessible residues differed from the human germline sequence and were adapted to the human version by substituting with their corresponding amino acids. As the foregoing criteria of coding, when according to the coding method of residue numbers defined by Kabat et al., the QBEND/10 $V_H$ was coded and the above-mentioned 4 amino acids were substituted as follows: the amino acid Glutamic acid at position 5 of Kabat's coded QBEND/10 $V_H$ was substituted with Valine (Gln5Val) (Glu5Val), the amino acid Proline at position 9 of Kabat's coded QBEND/10 $V_H$ was substituted with Alanine (Pro9Ala), the amino acid Lysine at position 73 of Kabat's coded QBEND/10 $V_H$ was substituted with Threonine (Lys73Thr), and the amino acid Glutamine at position 74 of Kabat's coded QBEND/10 $V_H$ was substituted with Serine (Gln74Ser).

Similarly, when according to the position of each amino acid of the $V_H$ sequence as shown in sequence listing, the above-mentioned 4 amino acids were substituted as follows: the amino acid Glutamic acid at position 5 of QBEND/10 $V_H$ was substituted with Valine (Glu5Val), the amino acid Proline at position 9 of QBEND/10 $V_H$ was substituted with Alanine (Pro9Ala), the amino acid Lysine at position 74 of QBEND/10 $V_H$ was substituted with Threonine (Lys74Thr), and the amino acid Glutamine at position 75 of QBEND/10 $V_H$ was substituted with Serine (Gln75Ser).

Figure 6A:
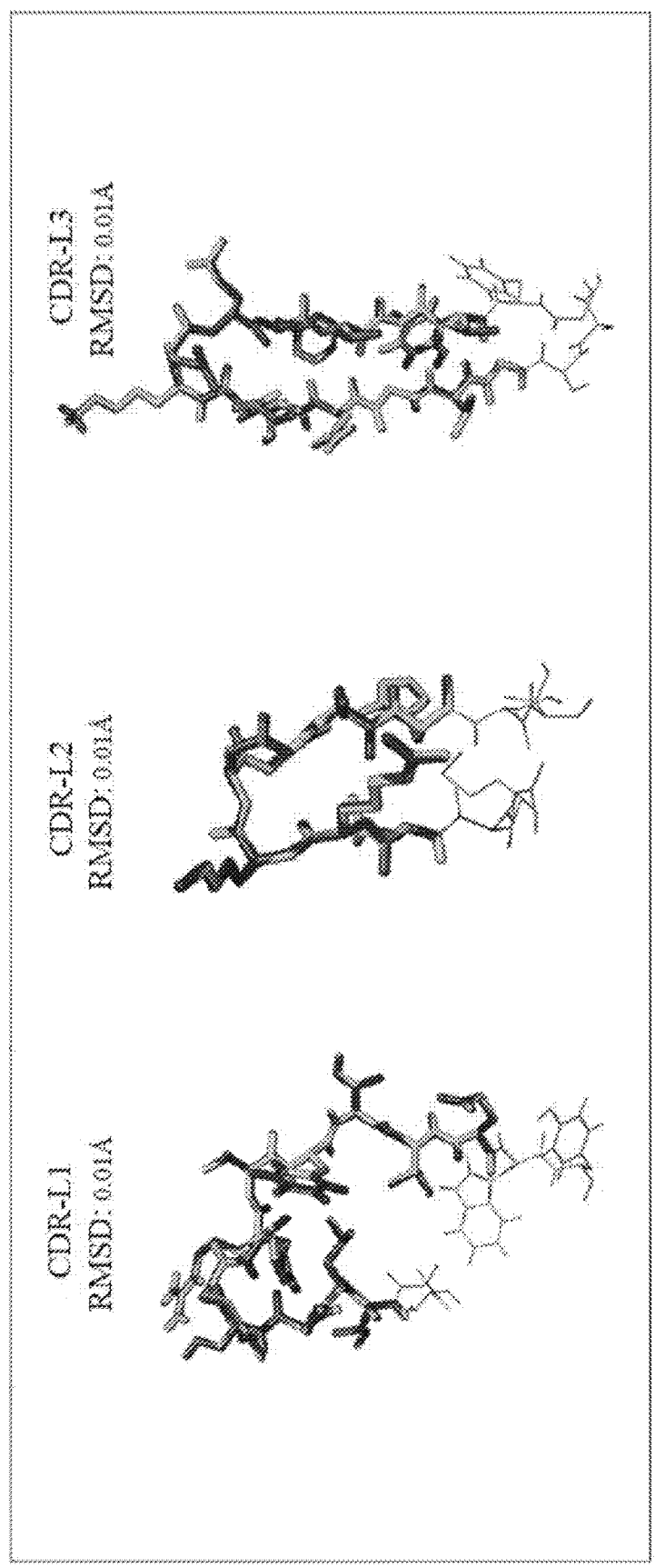
FIGS. 6A and 6B both show the structure homology models of resurfaced QBEND/10 CDRs versus mouse QBEND/10 CDRs. Resurfaced QBEND/10 CDRs marked in dark gray showed only minor differences in the loop structures in comparison to the mouse QBEND/10 CDRs marked in light gray.
Figure 6B:
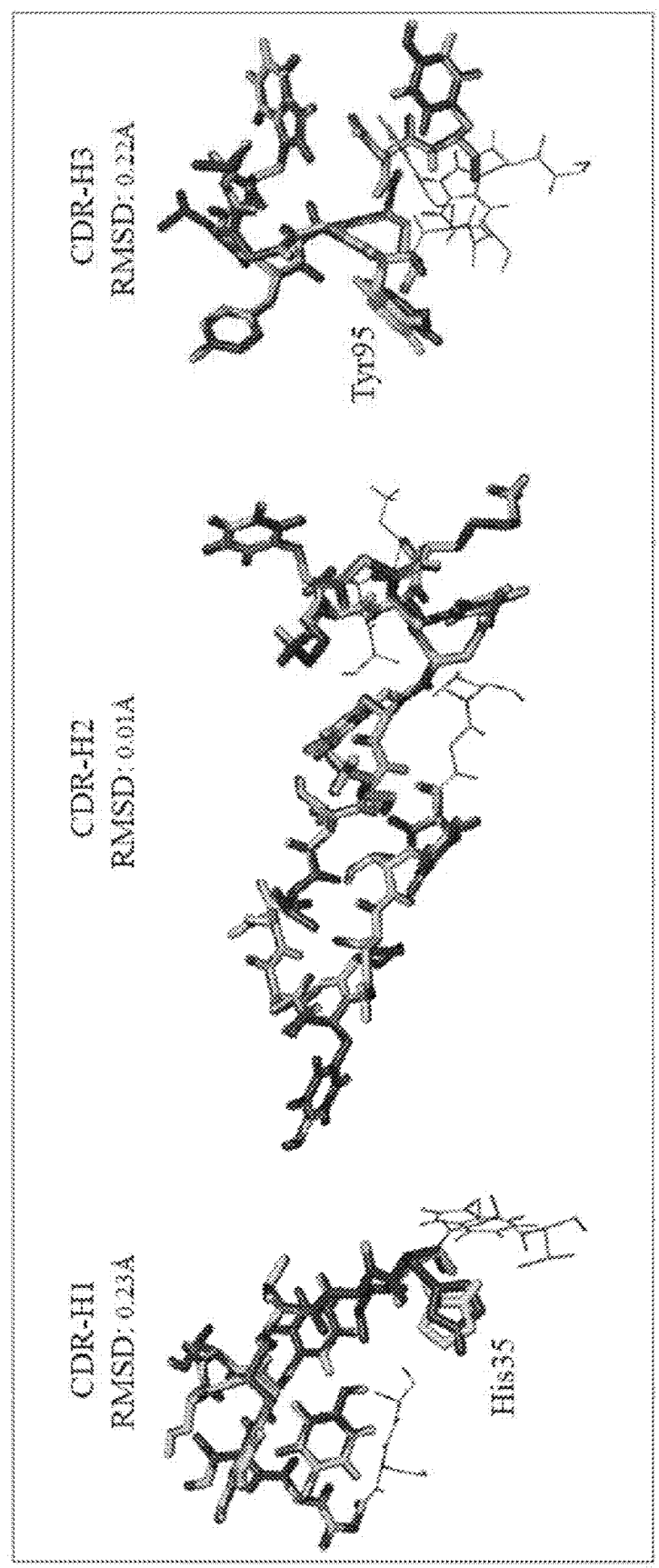

As depicted in FIGS. 6A and 6B, the models of the mouse and the resurfaced QBEND/10 were superimposed to determine the conformational changes in the CDR regions. By using the root-mean-square deviation (RMSD) (Maiorov V N, Crippen G M. Significance of root-mean-square deviation in comparing three-dimensional structures of globular proteins. Journal of molecular biology. 1994; 235(2):625-34), the similarity of these two three-dimensional structures were measured. In which, the RMSD value of zero means the two 3D structures are identical, but the high value RMSD means the conformation of the two 3D structures are different. Further, the RMSD value of <1.5 Å have been published for defining the accuracy of a comparative model (Baker D, Sali A. Protein structure prediction and structural genomics. Science. 2001; 294(5540):93-6). As shown in FIG. 6, the RMSD value ranging from 0.01 to 0.23 Å indicated that the mouse QBEND/10 model was similar to the resurfaced QBEND/10 model. The only differences between mouse and the resurfaced QBEND/10 model were observed in the loop of CDR-H1 (His35) and CDR-H3 (Tyr95). However, due to the low RMSD value, His35 and Tyr95 weren't considered to influence the correct CDR-H1 and CDR-H3 conformations.

5. Construction and Expression of QBEND/10

Figure 7:
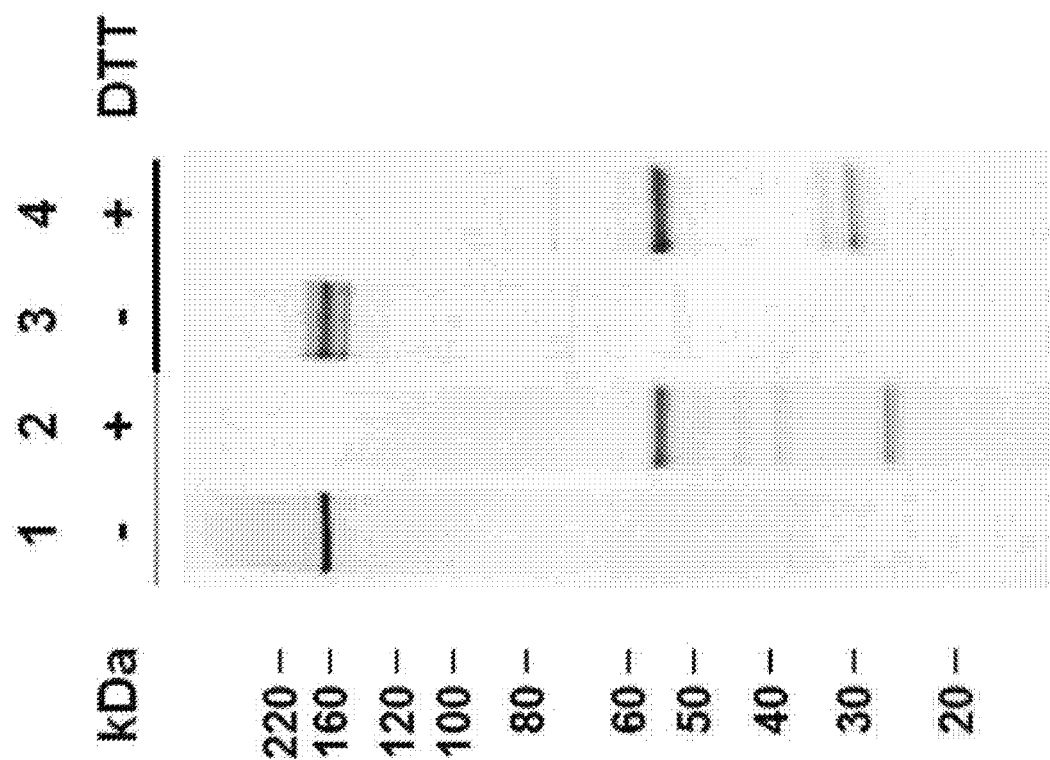
FIG. 7 shows the purification of chimeric and humanized QBEND/10 antibodies. The indicated chimeric QBEND/10 (lanes 1 and 2) and humanized QBEND/10 (lanes 3 and 4) antibodies were stably expressed in mouse myeloma NSO cells and purified from culture media by column chromatography. The samples were electrophoresed on a 4-12% NuPAGE Bis-Tris polyacrylamide gel with MOPS (3-morpholinopropanesulfonic acid) buffer under non-reducing conditions (lanes 1 and 3) and reducing conditions (lanes 2 and 4). Gel was stained with Coomassie Brilliant Blue.

In the disclosure, two mammalian expression vectors, pSecTag2/Hygro and pcDNA3.3, were used to express the intact QBEND/10 IgG molecule. In addition, a leader sequence was added upstream of the heavy chain and light chain, respectively, to make the expressed QBEND/10 to be secreted to the culture media. The amino acid sequences of QBEND/10 $V_H$ and $V_L$ were cloned in-frame with the human immunoglobulin gamma 1 heavy chain and lambda light chain constant regions, respectively. Further, chimeric and humanized QBEND/10 antibodies were expressed as soluble secretory proteins in mouse myeloma NSO cells. Each of the culture medium was purified using the human-IgG affinity column (IgSelect; GE Healthcare) and analyzed through SDS-PAGE. As shown in FIG. 7, one prominent band of approximately 150 kDa in non-reducing conditions and two clear bands of approximately 50 kDa (heavy chain) and approximately 25 kDa (light chain) in reducing conditions were observed.

6. Antibody Binding Analysis

The surface plasmon resonance (SPR) biosensor-based assay was performed to determine the binding affinities of the two antibodies, chimeric and humanized QBEND/10, with the recombinant human CD34 protein. At the same time, the binding kinetics were also determined. The results of binding affinities and binding kinetics were shown in Table 3 and FIGS. 8A and 8B.

TABLE 3

Binding kinetics of chimeric and humanized QBEND/10 to immobilized human CD34 protein

| Antibody | $k_{on}/10^4$ (M$^{-1}$ s$^{-1}$) | $k_{off}/10^{-4}$ (s$^{-1}$) | $K_D$ (nM) |
|---|---|---|---|
| chimeric QBEND/10 | 1.78 | 2.62 | 14.7 |
| humanized QBEND/10 | 3.66 | 2.68 | 7.34 |

Figure 8A:
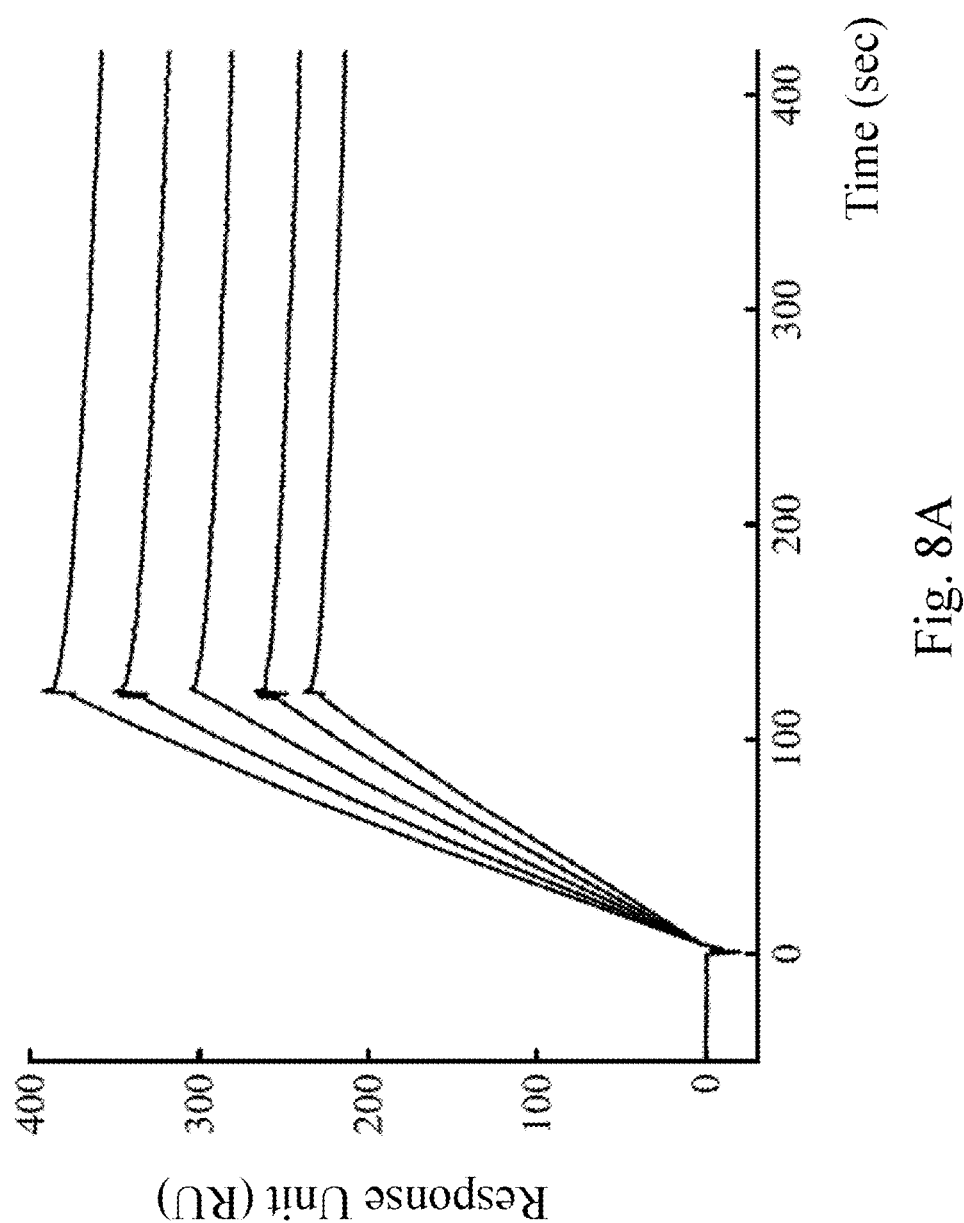
FIGS. 8A and 8B show the surface plasma resonance (SPR) analysis of interaction between human CD34 protein and chimeric QBEND/10 (A) or humanized QBEND/10 (B). Each antibody was injected and flowed over a surface chip with immobilized human CD34 protein at a flow rate of 30 μl/min. The resulting SPR sensorgrams were analyzed to determine the association/dissociation rate constants using the analysis program (BIAevaluation 3.2) provided by the manufacturer. Measured kinetic constants are summarized in Table 3.
Figure 8B:
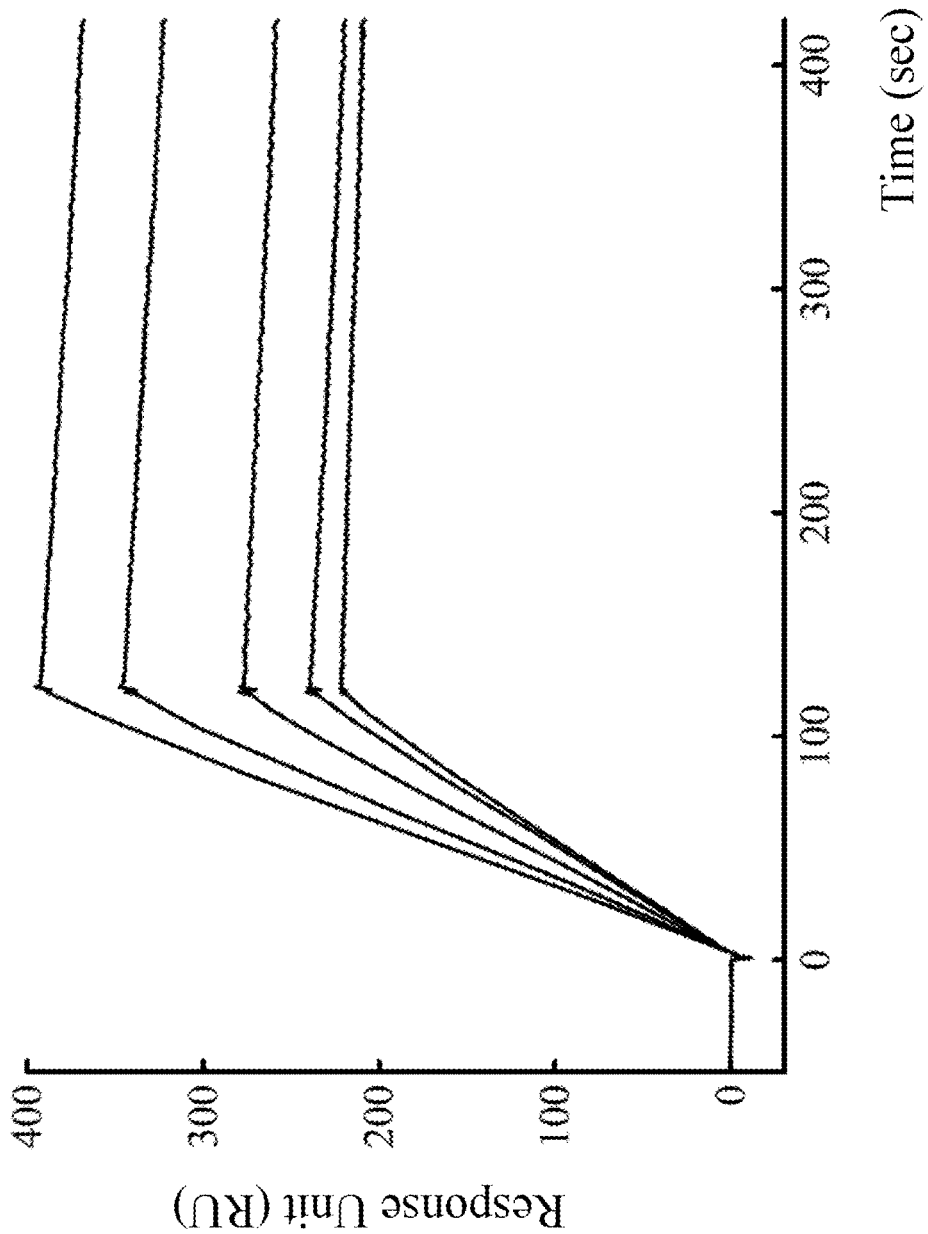

As illustrated in Table 3 and FIGS. 8A and 8B, the $K_D$ of the binding of chimeric QBEND/10 with human CD34 protein was 14.7 nM, whereas that of the humanized QBEND/10 with human CD34 protein was 7.34 nM. In both instances, the dissociation rate constant ($k_{off}$) was approximately $2.6 \times 10^{-4}$ s$^{-1}$, whereas the association rate constant ($k_{on}$) increased by two-fold for the humanized QBEND/10 (from $1.78 \times 10^4$ M$^{-1}$ s$^{-1}$ to $3.66 \times 10^4$ M$^{-1}$ s$^{-1}$) (referring to Table 3). The similar $K_D$ values in chimeric and humanized QBEND/10 indicated that the humanization process did not alter the binding affinity of the antibody to human CD34 protein. That is, the humanized antibody can retain the binding affinity similar to that of the parental antibody.

7. Effects of Humanized QBEND/10 on Endothelial Cell Tube Formation

Figure 9A:
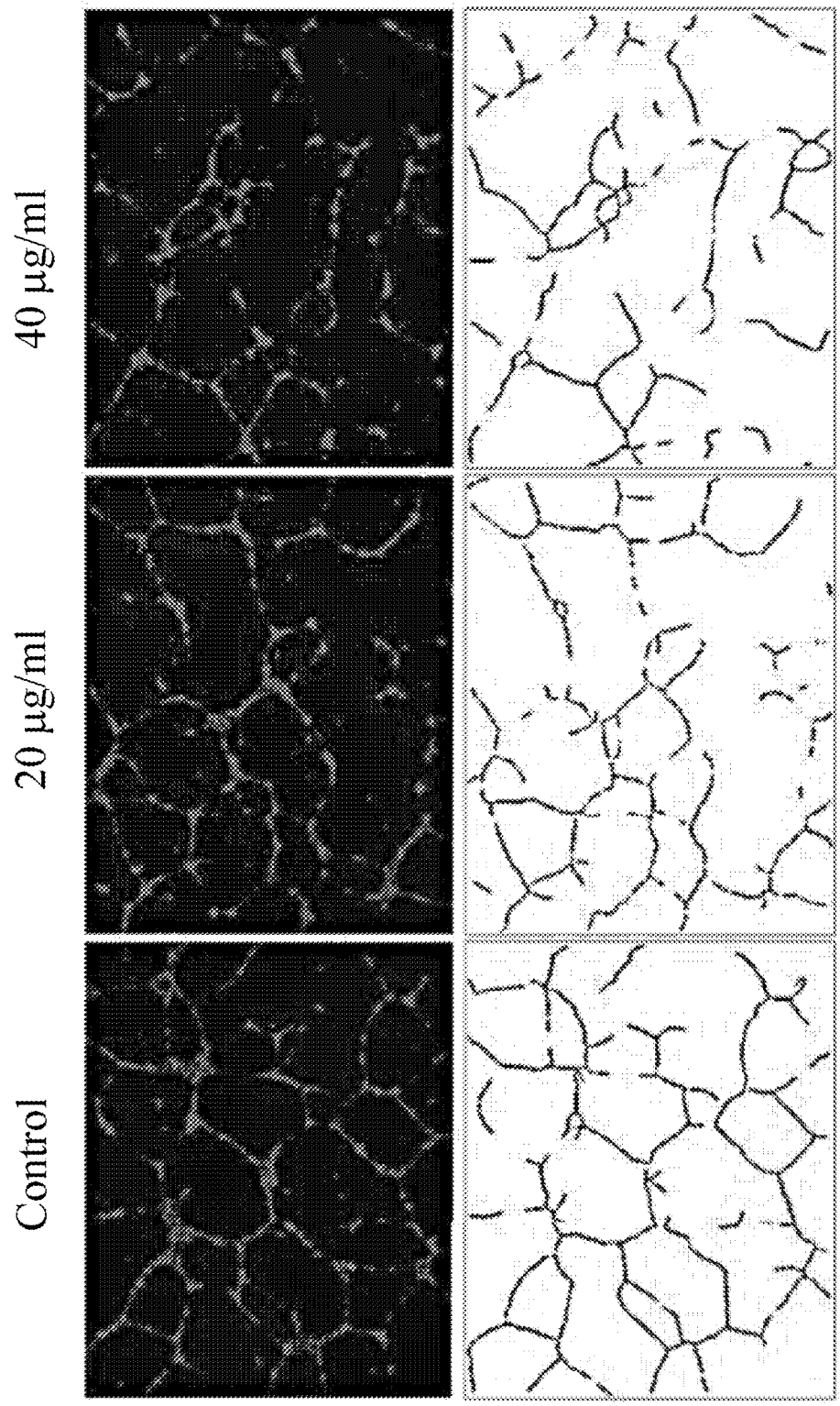
FIGS. 9A and 9B show the QBEND/10 impaired tube formation of human umbilical vascular endothelial cells. (A-top) Representative fluorescent image of tubular network on Matrigel formed by HUVECs in vitro in the presence of PBS (control), 20 μg/ml or 40 μg/ml of humanized QBEND/10. (A-bottom) ImageJ plugin analyzed binary tree of HUVECs network. (B) Quantification of tube length per field from FIG. 9A. One field was examined per well, with five wells per dose, per experiment. In which, * represents $p<0.05$, 40 μg/ml of QBEND/10 compared to control.
Figure 9B:
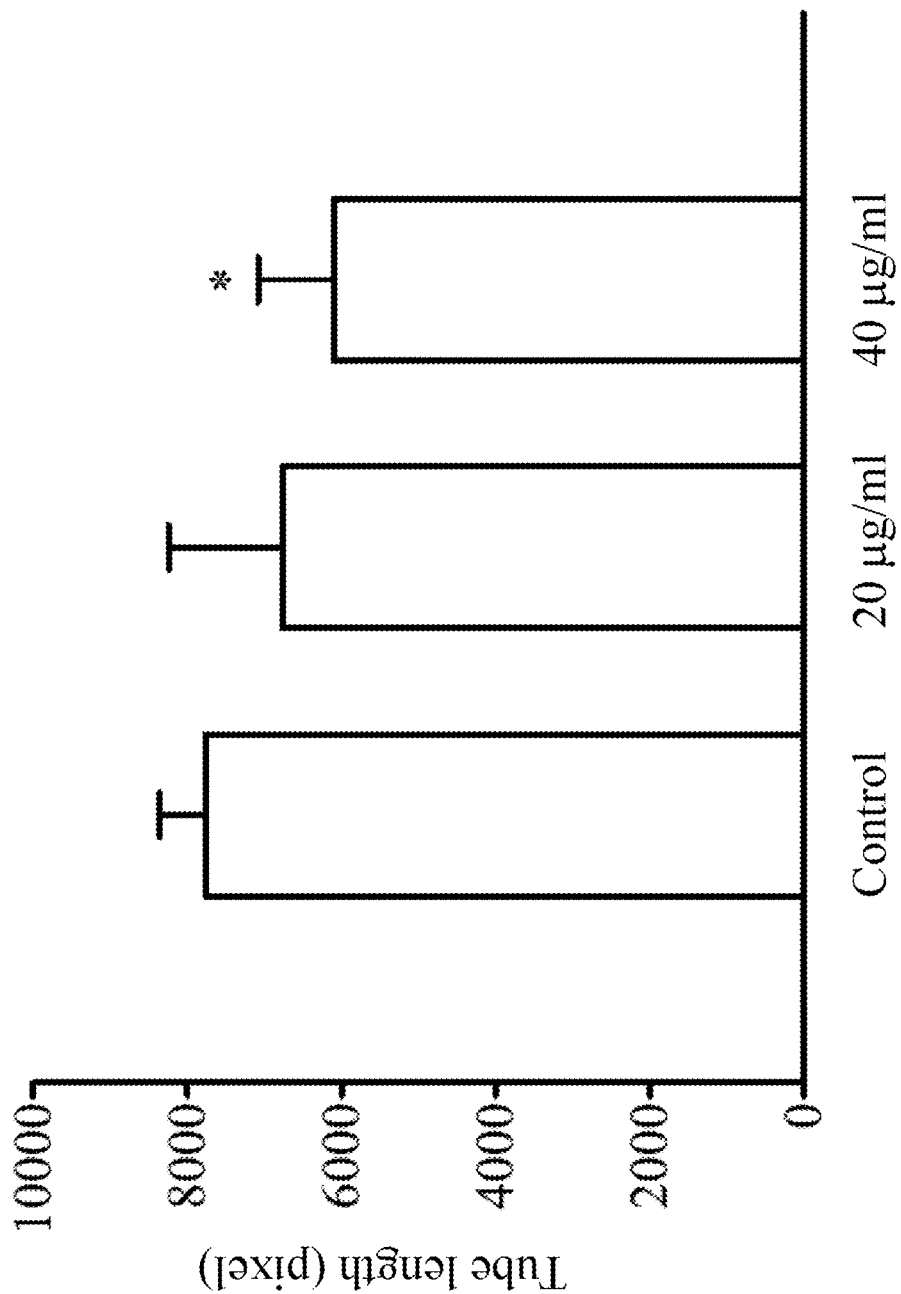

Referring to FIGS. 9A and 9B, the tube-forming network was significantly reduced when 40 μg/ml humanized QBEND/10 was applied to the culture compared to control cells (* represents p<0.05). Moreover, as illustrated in FIG. 9B, the tube formation of HUVECs was impaired by humanized QBEND/10 in a dose-dependent manner. That is, the inhibitory effect on the tube formation of HUVECs is more significant with the increase in the dose of the humanized QBEND/10.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A humanized monoclonal antibody, comprising:
a light chain variable region comprising an amino acid sequence as set forth in SEQ ID NO: 1; and
a heavy chain variable region comprising an amino acid sequence as set forth in SEQ ID NO: 2;
wherein the amino acid sequence of SEQ ID NO: 1 and the amino acid sequence of SEQ ID NO: 2 have at least one substitution selected from a group consisting of the following:
the amino acid Serine at position 8 of SEQ ID NO: 1 is substituted with Proline (Ser8Pro);
the amino acid Leucine at position 41 of SEQ ID NO: 1 is substituted with Glutamic acid (Leu41Glu);
the amino acid Threonine at position 58 of SEQ ID NO: 1 is substituted with Lysine (Thr58Lys);
the amino acid Asparagine at position 81 of SEQ ID NO: 1 is substituted with Serine (Asn81Ser);
the amino acid Glycine at position 108 of SEQ ID NO: 1 is substituted with Threonine (Gly108Thr);
the amino acid Glutamic acid at position 5 of SEQ ID NO: 2 is substituted with Valine (Glu5Val);
the amino acid Proline at position 9 of SEQ ID NO: 2 is substituted with Alanine (Pro9Ala);
the amino acid Lysine at position 74 of SEQ ID NO: 2 is substituted with Threonine (Lys74Thr); and
the amino acid Glutamine at position 75 of SEQ ID NO: 2 is substituted with Serine (Gln75Ser).

2. The humanized monoclonal antibody as claimed in claim 1, wherein the light chain variable region comprises the amino acid sequence as set forth in SEQ ID NO: 9 and the heavy chain variable region comprises the amino acid sequence as set forth in SEQ ID NO: 10.

3. The humanized monoclonal antibody as claimed in claim 1, wherein the humanized monoclonal antibody comprises a solid support, functional group or biomolecule.

4. The humanized monoclonal antibody as claimed in claim 3, wherein the solid support comprises a bead, chip or plate.

5. The humanized monoclonal antibody as claimed in claim 3, wherein the functional group comprises an amino group (—NH2), mercapto group (—SH), carboxyl group (—COOH) or hydroxyl group (—OH).

6. The humanized monoclonal antibody as claimed in claim 3, wherein the biomolecule comprises a biotin, avidin or streptavidin.

7. The humanized monoclonal antibody as claimed in claim 1, wherein the humanized monoclonal antibody comprises a color material.

8. The humanized monoclonal antibody as claimed in claim 7, wherein the color material comprises a fluorochrome, fluorescent protein, bioluminescence, or nanoparticles.

9. The humanized monoclonal antibody as claimed in claim 1, wherein the antibody binds to human CD34 antigen.

10. A humanized monoclonal antibody, comprising:
a light chain variable region; and
a heavy chain variable region;
wherein the light chain variable region is encoded by a nucleotide sequence which encodes an amino acid sequence as set forth in SEQ ID NO: 9, and the heavy chain variable region is encoded by a nucleotide sequence which encodes an amino acid sequence as set forth in SEQ ID NO: 10; and
wherein the humanized monoclonal antibody binds to a CD34 antigen.

11. The humanized monoclonal antibody as claimed in claim 10, wherein the humanized monoclonal antibody comprises a solid support, functional group or biomolecule.

12. A humanized monoclonal antibody, comprising:
a light chain variable region; and
a heavy chain variable region;
wherein the light chain variable region is encoded by a nucleotide sequence as set forth in SEQ ID NO: 13, and the heavy chain variable region is encoded by a nucleotide sequence as set forth in SEQ ID NO: 14; and
wherein the humanized monoclonal antibody binds to a CD34 antigen.

13. The humanized monoclonal antibody as claimed in claim 12, wherein the humanized monoclonal antibody comprises a solid support, functional group or biomolecule.

14. A method for treating angiogenesis and/or angiogenesis-related disease, comprising:
administering an effective amount of the humanized monoclonal antibody as claimed in claim 1 to a subject in need thereof to treat angiogenesis and/or angiogenesis-related disease.

15. The method as claimed in claim 14, wherein the light chain variable region comprises the amino acid sequence as set forth in SEQ ID NO: 9 and the heavy chain variable region comprises the amino acid sequence as set forth in SEQ ID NO: 10.

16. The method as claimed in claim 14, wherein the angiogenesis-related disease is cancer, neovascular glaucoma or age-related macular degeneration (AMD or ARMD).

* * * * *